United States Patent
Sahade

(10) Patent No.: US 8,535,769 B2
(45) Date of Patent: Sep. 17, 2013

(54) POLYMERIZABLE LIQUID CRYSTAL COMPOUND, POLYMERIZABLE LIQUID CRYSTAL COMPOSITION, AND ORIENTED FILM

(75) Inventor: Daniel Antonio Sahade, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 6 days.

(21) Appl. No.: 13/496,229

(22) PCT Filed: Sep. 16, 2010

(86) PCT No.: PCT/JP2010/066013

§ 371 (c)(1),
(2), (4) Date: Mar. 15, 2012

(87) PCT Pub. No.: WO2011/034118

PCT Pub. Date: Mar. 24, 2011

(65) Prior Publication Data

US 2012/0172560 A1   Jul. 5, 2012

(30) Foreign Application Priority Data

Sep. 16, 2009   (JP) .................................. 2009-214661

(51) Int. Cl.
- *C09K 19/34* (2006.01)
- *C09K 19/12* (2006.01)
- *C09K 19/20* (2006.01)
- *C07D 307/33* (2006.01)
- *C08F 24/00* (2006.01)
- *G02F 1/1337* (2006.01)

(52) U.S. Cl.
USPC ... 428/1.1; 428/1.2; 252/299.61; 252/299.66; 252/299.67; 549/323; 526/270

(58) Field of Classification Search
USPC .................. 428/1.1, 1.2; 252/299.61, 299.66, 252/299.67; 549/323; 526/270
See application file for complete search history.

(56) References Cited

U.S. PATENT DOCUMENTS

| | | | |
|---|---|---|---|
| 4,810,433 A | 3/1989 | Takayanagi et al. | |
| 6,696,217 B2 | 2/2004 | Yoon et al. | |
| 7,862,867 B2 * | 1/2011 | Sahade ......................... | 428/1.1 |
| 2009/0088545 A1 | 4/2009 | Sahade et al. | |
| 2010/0044632 A1 | 2/2010 | Sahade | |

FOREIGN PATENT DOCUMENTS

| | | |
|---|---|---|
| EP | 2062882 A1 | 5/2009 |
| JP | 62-70407 A | 3/1987 |
| JP | 9-208957 A | 8/1997 |
| JP | 9-241249 A | 9/1997 |
| JP | 2002-308937 A | 10/2002 |
| WO | WO 2006/115112 A1 | 11/2006 |
| WO | WO 2008/044536 A1 | 4/2008 |
| WO | WO 2008/072652 A1 | 6/2008 |
| WO | WO 2010/044384 A1 | 4/2010 |

OTHER PUBLICATIONS

International Search Report issued in PCT/JP2010/066013, dated Dec. 7, 2010.
Ramarajan et al., "Ethyl Alpha-(Bromomethyl)Acrylate (2-Propenoic acid, 2-(bromomethyl)-,ethyl ester)," Organic Syntheses, 1983, vol. 61, pp. 56-59.
Talaga et al., "A New Synthesis of Gamma-Substituted Alpha-Methylene-Gamma-butyrolactones (2-Methylene-4-alkanolides) using Catalysis by SnCl2/Amberlyst 15," Synthesis, 1990, p. 530.
Written Opinion of the International Searching Authority issued in PCT/JP2010/066013, dated Dec. 7, 2010.

* cited by examiner

*Primary Examiner* — Shean C Wu
(74) *Attorney, Agent, or Firm* — Birch, Stewart, Kolasch & Birch, LLP

(57) ABSTRACT

Since a polymerizable liquid crystal compound represented by the general formula (1) produces polymers exhibiting high optical anisotropy and high chemical resistance, and the optical anisotropy thereof exhibits low wavelength dependence, polymers obtained from a polymerizable liquid crystal composition comprising said polymerizable liquid crystal compound are useable as an optically anisotropic film for polarizers, wave plates, and the like, and are particularly best used in pattern formation that uses photolithography in air.

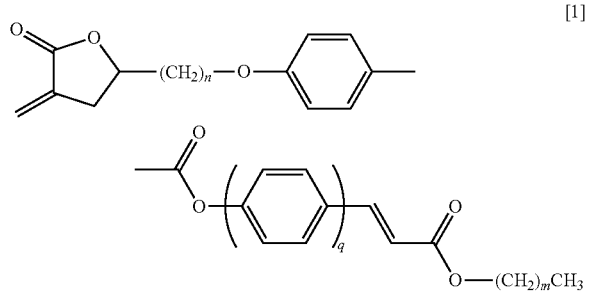

[1]

(n represents an integer in the range of 3 to 10, m represents an integer in the range of 0 to 5, and q represents an integer in the range of 1 to 2.)

10 Claims, No Drawings

POLYMERIZABLE LIQUID CRYSTAL COMPOUND, POLYMERIZABLE LIQUID CRYSTAL COMPOSITION, AND ORIENTED FILM

TECHNICAL FIELD

This invention relates to a polymerizable liquid crystal compound having polymerizability and liquid crystal properties, a composition including the same, and a polymer obtained therefrom and more particularly, to a polymerizable liquid crystal compound, a composition including the same and a polymer obtained by use thereof, which can be appropriately utilized, for example, as display devices and materials having optical characteristics, such as recording materials, particularly, as optical compensation films such as a polarizer, a wave plate and the like for a liquid crystal display.

BACKGROUND ART

Because of the requirements for an improvement of display quality of liquid crystal display devices and weight saving thereof, there has been increasing a demand of a polymer film whose inner molecular orientation structure is controlled for use as an optical compensation film such as a polarizer, a wave plate or the like. In order to meet the above demand, films making use of optical anisotropy of polymerizable liquid crystal compounds have been developed.

The polymerizable liquid crystal compounds used herein are generally those liquid crystal compounds having both a polymerizable group and liquid crystal structural units (i.e. structural units having a spacer moiety and a mesogenic moiety), in which an acrylic group has been widely used as the polymerizable group.

In general, such polymerizable liquid crystal compounds are converted to polymers (films) according to a method of polymerization by irradiation of a radiation such as UV light or the like.

For instance, there are known methods including a method wherein a specific type of polymerizable liquid crystal compound having an acrylic group is held between supports and a radiation is irradiated while keeping the compound in liquid crystal state (see Patent Document 1) and a method wherein a photopolymerizable initiator is added to a mixture of two types of polymerizable liquid crystal compounds having an acrylic group or a composition obtained by further mixing a chiral liquid crystal compound with the mixture, followed by irradiation of UV light to obtain a polymer (see Patent Document 2).

The polymers (films) obtained by the above methods have been used, as a film for polarizer or wave plate, not only in display devices such as a monitor and television set, but also in display devices employed in a high temperature environment such as of automobiles. To this end, to keep transparency under high temperature environment is very important for use as a display device material.

Recently, in the field of displays, investigations for process simplification making use of these materials as an in-cell phase difference film have been actively conducted. As to the materials used in the in-cell technique, higher thermal stability and chemical resistance have been required.

On the other hand, when compared with optical anisotropic films obtained from other processes (e.g. stretching of polyvinyl alcohol films), the films obtained from polymerizable liquid crystal compounds have a problem in that the optical anisotropy thereof is lower in wavelength dependence.

PRIOR ART DOCUMENTS

Patent Documents

Patent Document 1: JP-A S62-70407
Patent Document 2: JP-A H09-208957

SUMMARY OF THE INVENTION

Problems to be Solved by the Invention

The present invention has been made under such circumstances as set out above and has for its object the provision of a polymerizable liquid crystal compound that has excellent optical anisotropy and is able to provide a film exhibiting a chemical resistance, a polymerizable liquid crystal composition including the compound, and a polymer and oriented film thereof.

Means for Solving the Problems

The present inventors have made intensive studies so as to solve the above problems and, as a result, found that a certain type of polymerizable liquid crystal compound having an α-methylene-γ-butyrolactone moiety and a cinnamate moiety has liquid crystal properties, is excellent in self-polymerizability and is able to provide a stable polymerizable liquid crystal composition, and the polymer or film obtained from the polymerizable liquid crystal composition has an excellent chemical resistance in the optical anisotropy, thereby arriving at completion of the present invention.

More particularly, the present invention provides:
1. A polymerizable liquid crystal compound, characterized by being represented by the following formula [1]:

[Chemical Formula 1]

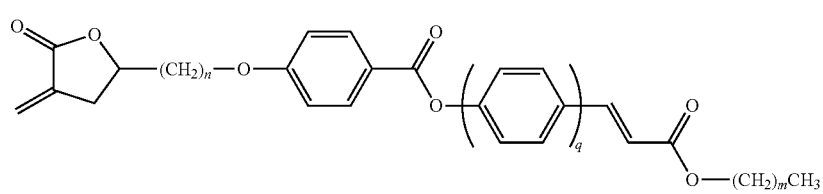

[1]

wherein n is an integer of 3 to 10, m is an integer of 0 to 5, and q is an integer of 1 to 2;

2. A polymerizable liquid crystal composition including the polymerizable liquid crystal compound of 1;

3. The polymerizable liquid crystal composition of 2, further including a liquid crystal compound having at least one polymerizable group in the molecule;

4. The polymerizable liquid crystal composition of 3, wherein said liquid crystal compound is a compound having at least one polymerizable group represented by the following formula [2] or [3] in the molecule;

[Chemical Formula 2]

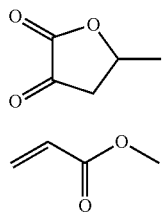
[2]

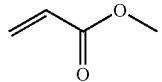
[3]

5. The polymerizable liquid crystal composition of 3 or 4, wherein said liquid crystal compound is at least one selected from the group consisting of compounds represented by the following formula [4]:

[Chemical Formula 3]

[4]

in which X is a fluorine atom, a cyano group or a monovalent hydrocarbon group having 4 to 8 carbon atoms, f represents an integer of 2 to 9, and M is a group represented by the following formula [2] or [3];

[Chemical Formula 4]

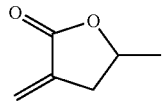
[2]

-continued

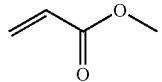
[3]

6. A polymer obtained from the polymerizable liquid crystal composition of any of 2 to 5;

7. A film obtained from the polymerizable liquid crystal composition of any of 2 to 5;

8. An oriented film obtained from the polymerizable liquid crystal composition of any of 2 to 5; and 9. An optical device including the polymer of 6 or the oriented film of 8.

Advantageous Effect of the Invention

The polymerizable liquid crystal compound of the present invention and the polymerizable liquid crystal composition including the compound are able to provide polymers exhibiting high optical anisotropy and high chemical resistance along with their optical anisotropy exhibiting low wavelength dependence.

Accordingly, the polymer obtained from the polymerizable liquid crystal composition including the polymerizable liquid crystal compound is utilizable as an optical anisotropic film such as of a polarizer, a wave plate or the like and particularly, can be conveniently employed for pattern formation using photolithography in the air.

EMBODIMENT FOR CARRYING OUT THE INVENTION

The terminologies used herein are as follows.

"Polymerizable liquid crystal compound" means a compound that has a polymerizable moiety such as an acrylic group; an α-methylenelactone ring or the like in the molecule and shows a liquid crystalline phase. "Liquid crystal composition" means a composition having such characteristics as showing a liquid crystalline phase. "Liquid crystal properties" means showing a liquid crystalline phase.

The present invention is now described in more detail.

[Polymerizable Liquid Crystal Compound]

The polymerizable liquid crystal compound according to the present invention is represented by the following formula [1]

[Chemical Formula 5]

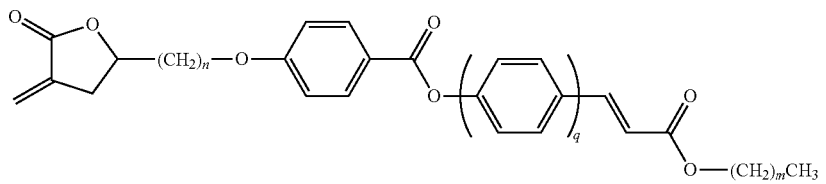
[1]

The compound represented by the formula [1] is a compound having liquid crystal properties and is also a polymerizable liquid crystal compound having an α-methylene-γ-butyrolactone moiety.

The α-methylene-γ-butyrolactone shows such a very excellent effect that it is less influenced by steric hindrance among α-alkylidene-γ-butyrolactones and has high polymerizability. This compound is effective to impart high Tg and a heat resistance to the polymer obtained by use of the compound.

In the formula [1], repeating units of the methylene group is a moiety called a so-called spacer moiety. In the formula, n represents the number of repetitions of the methylene group and is an integer of 3 to 10, preferably an integer of 4 to 6. m represents the number of repetitions of the methylene group and is an integer of 0 to 5, preferably an integer of 0 to 1. q represents the number of repetitions of the phenyl group and is an integer of 1 to 2, preferably 1.

The polymerizable liquid crystal compound represented by the above formula [1] exhibits a liquid crystalline phase including a smectic phase or a nemactic phase. This characteristic is useful in the fields of applications utilizing optical anisotropy, such as of a polarizer, a wave plate and the like.

Specific examples of the polymerizable liquid crystal compound represented by the formula [1] include those compounds of the formulas (1) to (29) indicated below although not limited thereto.

[Chemical Formula 6]

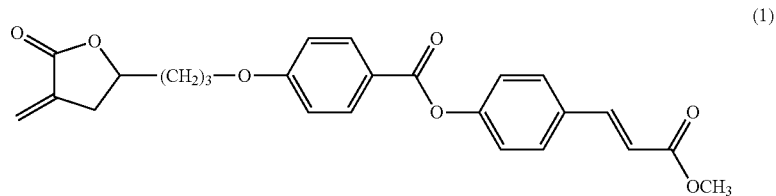
(1)

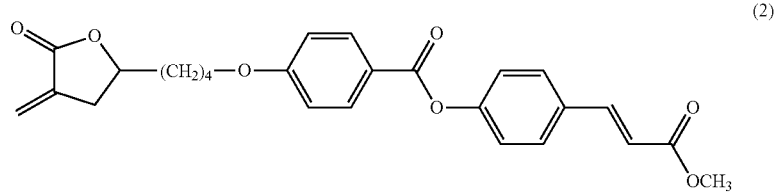
(2)

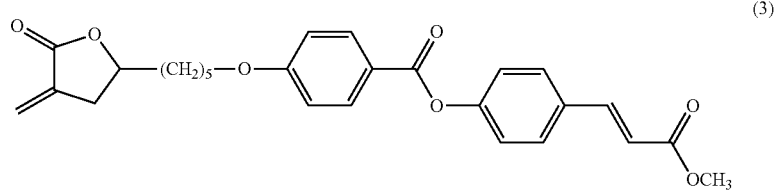
(3)

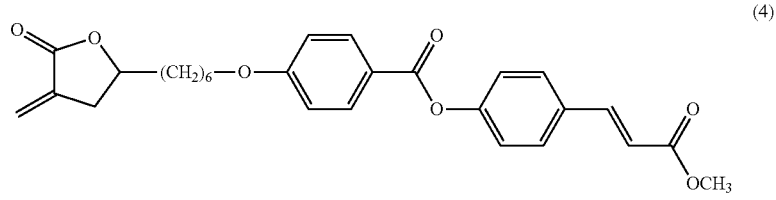
(4)

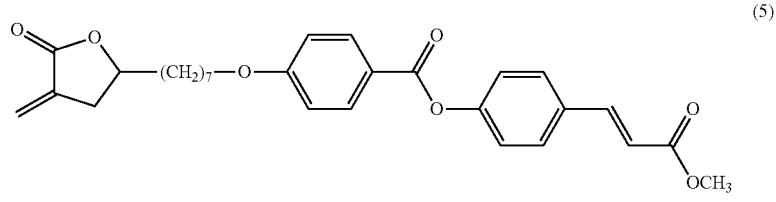
(5)

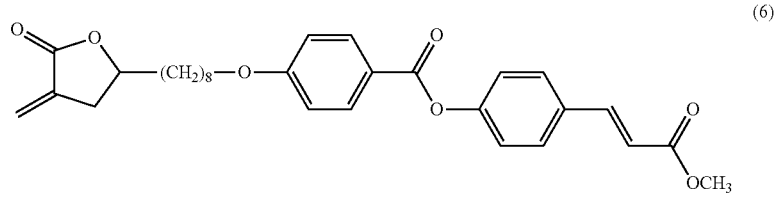
(6)

[Chemical Formula 7]

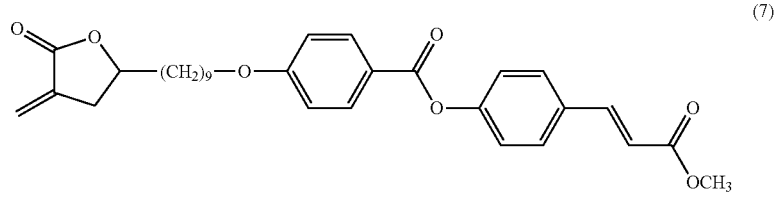
(7)

-continued
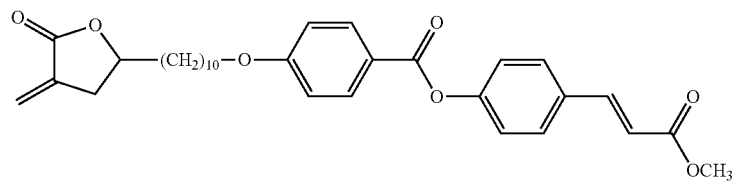
(8)
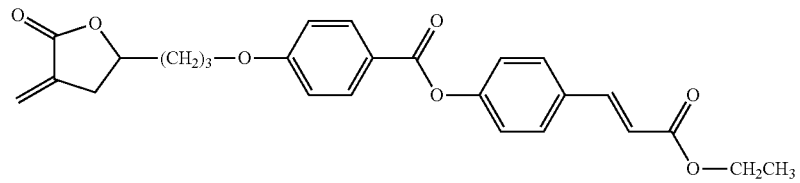
(9)
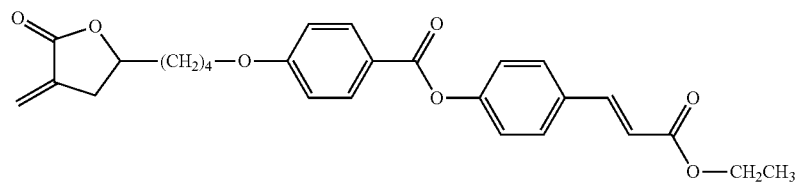
(10)
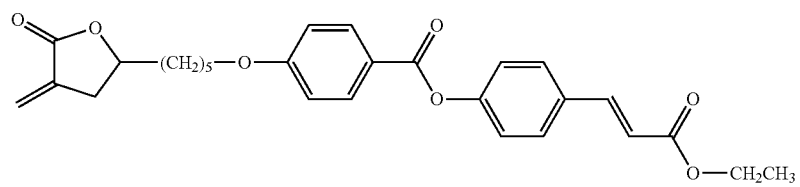
(11)
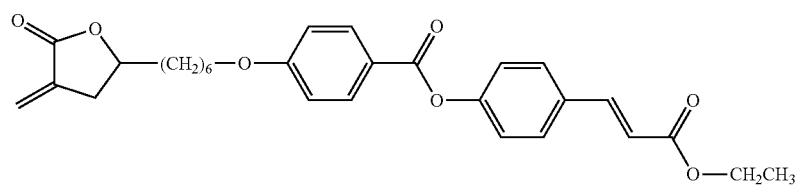
(12)
[Chemical Formula 8]
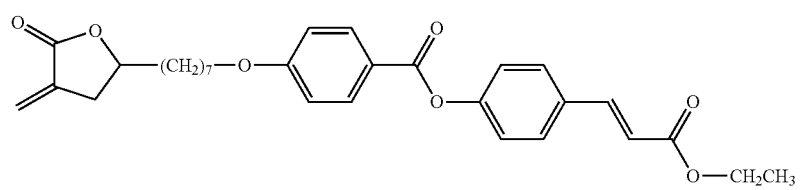
(13)
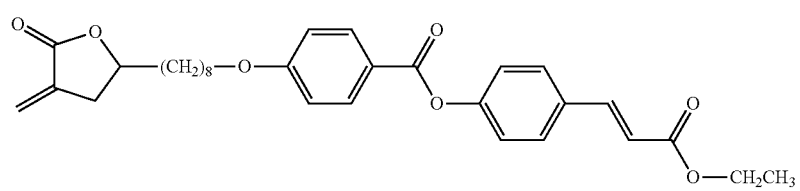
(14)
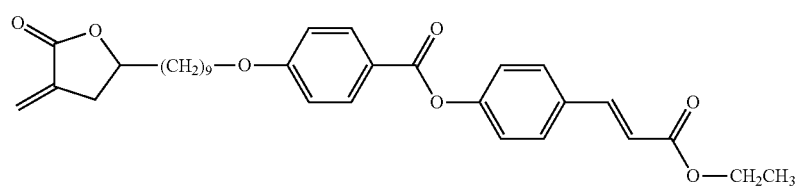
(15)

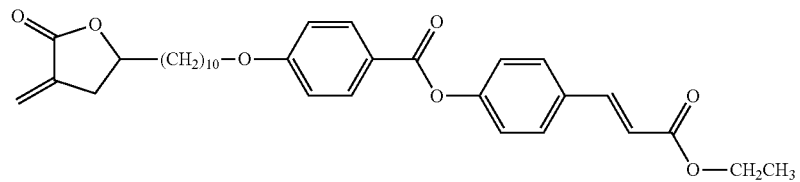
(16)
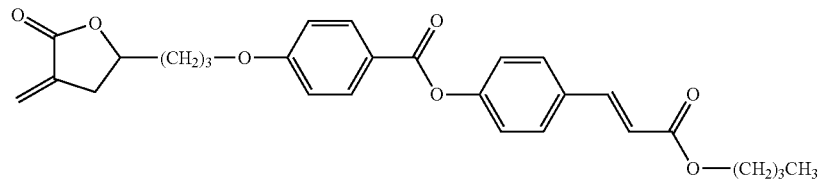
(17)
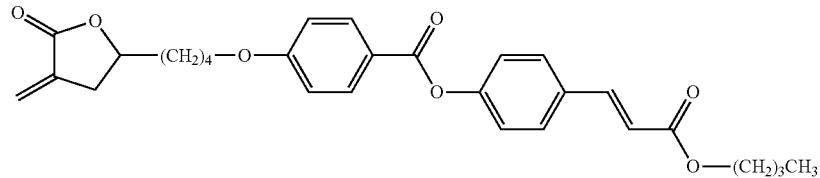
(18)
[Chemical Formula 9]
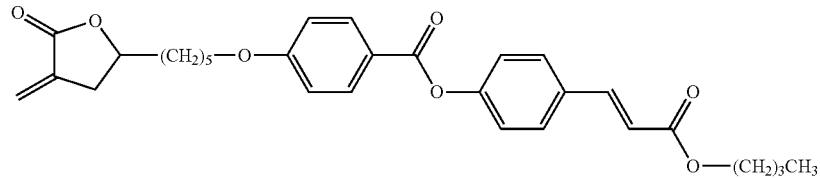
(19)
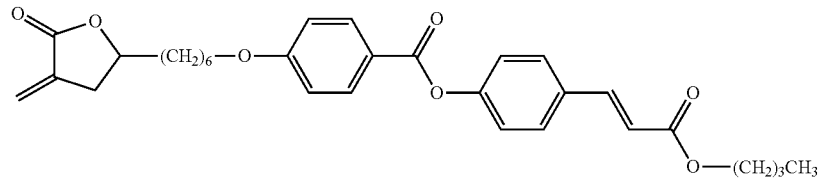
(20)
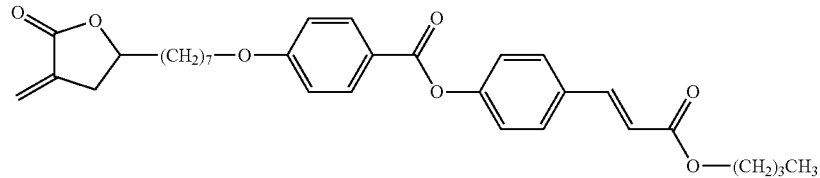
(21)
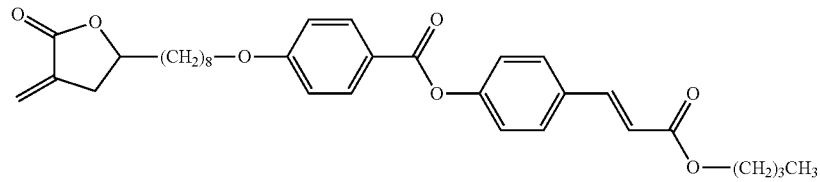
(22)
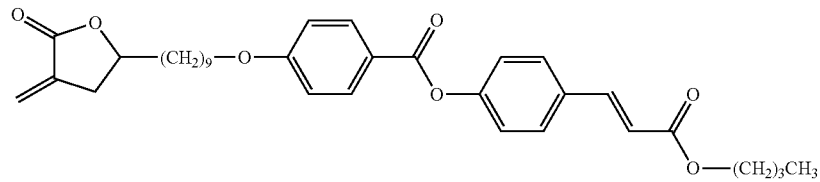
(23)

(24)
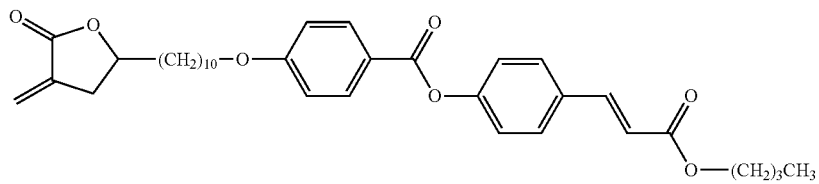

[Chemical Formula 10]

(25)
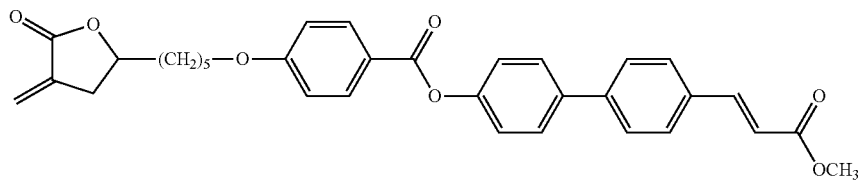

(26)
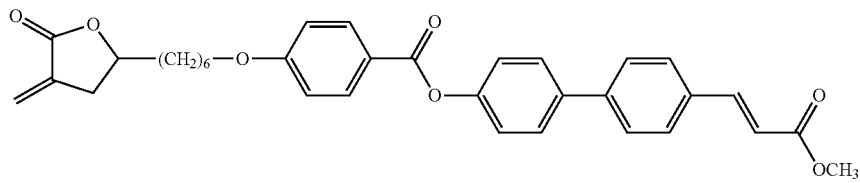

(27)
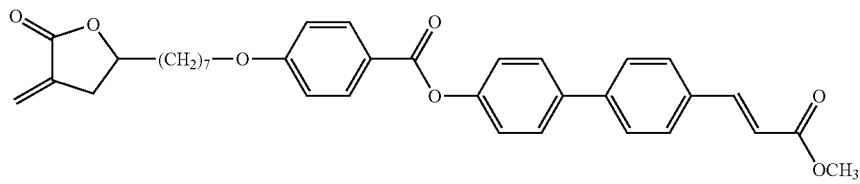

(28)
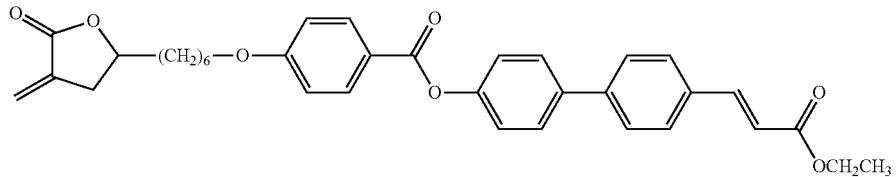

(29)
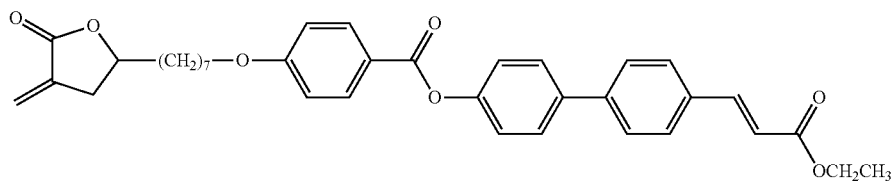

[Synthesis of Polymerizable Liquid Crystal Compound]

The polymerizable liquid crystal compound of the present invention can be synthesized according to a combination of techniques in the organic synthetic chemistry although no limitation is placed on its synthetic processes.

The compound having an α-methylene-γ-butyrolactone structure can be prepared according to the technique that is represented, for example, by the following synthetic scheme (A1) and proposed by P. Talaga et al (P. Talaga, M. Schaeffer, C. Benezra and J. L. Stampf, Synthesis, 530 (1990)). This technique is a process wherein 2-(bromomethyl)acrylic acid (2-(bromomethyl)propenoic acid) and an aldehyde or ketone are reacted by use of $SnCl_2$.

It will be noted that 2-(bromomethyl)acrylic acid (2-(bromomethyl)propenoic acid) can be obtained according to a process proposed by K. Ramarajan et al (K. Ramarajan, K. Kamalingam, D. J. O'Donnell and K. D. Berlin, Organic Synthesis, vol. 61, 56-59 (1983)).

[Chemical Formula 11]

(A1)
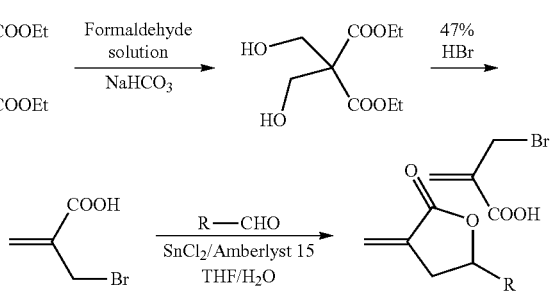

In the formula, R represents a monovalent organic group, and Amberlyst 15 is a registered tradename of Rohm and Haas Company.

For the reaction of 2-(bromomethyl)acrylic acid (2-(bromomethyl)propenoic acid) by use of $SnCl_2$, an acetal or ketal corresponding to the aldehyde or ketone may be used instead thereof to obtain an α-methylene-γ-butyrolactone structure.

As the acetal or ketal, mention is made of a dimethylacetal group, a diethylacetal group, a 1,3-dioxane group, a 1,3-dioxolane group and the like. The synthetic process and protective group are indicated in the following scheme (A2).

[Chemical Formula 12]

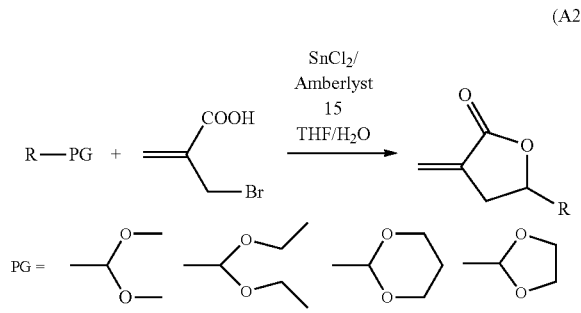

According to the technique of the following synthetic scheme (B) that is an application of the technique of the foregoing synthetic scheme (A1), the compound (intermediate) represented by the formula [2] can be synthesized.

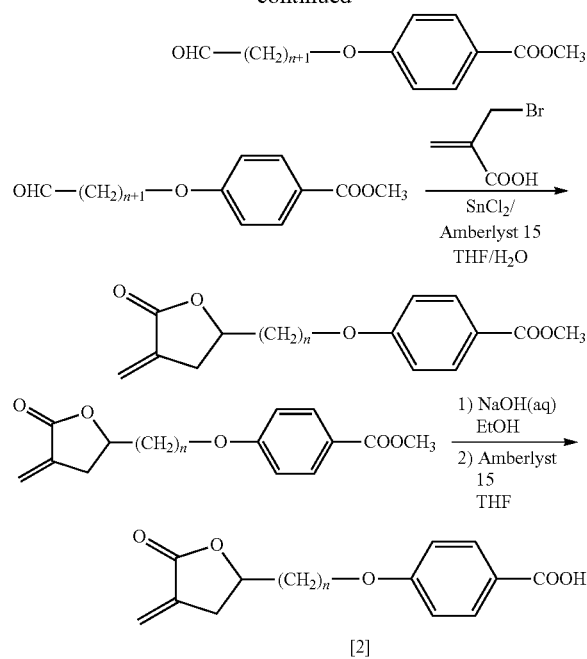

In the formula, n has the same meaning as defined before.

The compound represented by the above formula [2] can be converted to the compound represented by the formula [1] according to an esterification reaction with a phenolic compound as shown in the following synthetic scheme (C).

[Chemical Formula 14]

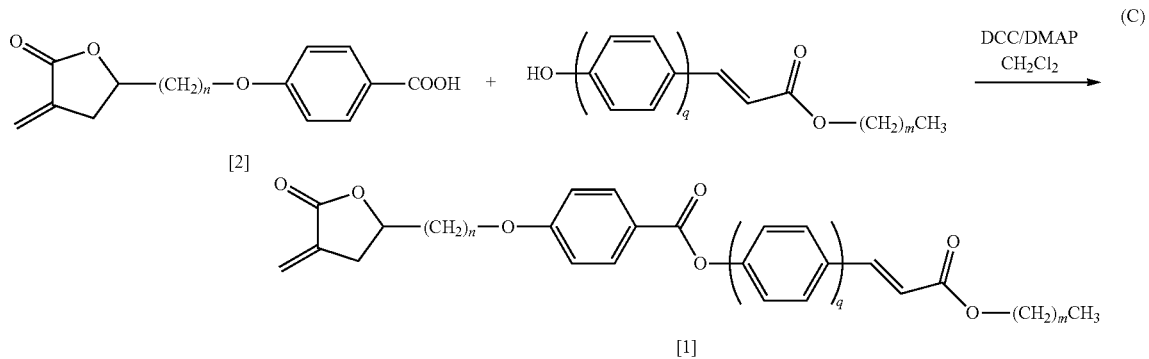

In the formula, n, m and q, respectively, have the same meanings as defined before.

[Polymerizable Liquid Crystal Composition]

The polymerizable liquid crystal composition of the present invention includes at least one polymerizable liquid crystal compound represented by the foregoing formula [1]. In the polymerizable liquid crystal composition of the present invention, where at least two polymerizable liquid crystal compounds represented by the formula [1] are used, polymerizable liquid crystal compounds may be appropriately chosen and mixed together, and a combination thereof may be arbitrary.

With the polymerizable liquid crystal composition of the present invention, a compound having a liquid crystal structural moiety (hereinafter referred to as specified compound)

[Chemical Formula 13]

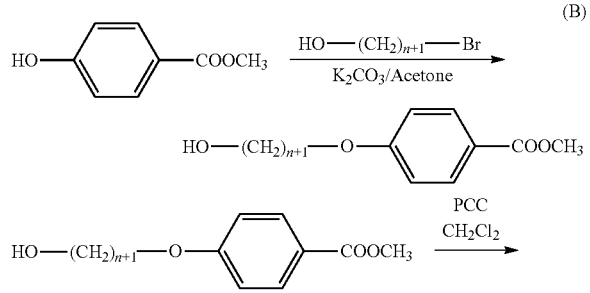

may be admixed with the polymerizable liquid crystal compound of the foregoing formula [1]. The specified compounds to be mixed may be used in combination of a plurality thereof.

The specified compound may be either a compound showing liquid crystal properties or a compound not showing liquid crystal properties, or may have or may not have a polymerizable group such as an acrylic group, a lactone group or the like. The specified compound having a polymerizable group may be either monofunctional or polyfunctional.

Such specified compounds include a compound having no polymerizable group but showing liquid crystal properties, a compound having no polymerizable group and showing no liquid crystal properties, a compound having a polymerizable group and showing liquid crystal properties but other than the polymerizable liquid crystal compound of the present invention, and a compound having a polymerizable group but showing no liquid crystal properties.

The mixing ratio of such a specified compound is not particularly limited. If a specified compound showing liquid crystal properties is mixed, its amount is preferably 900 to 5 parts by weight, more preferably 200 to 15 parts by weight, per 100 parts by weight of the polymerizable liquid crystal compound of the formula [1].

On the other hand, where a specified compound to be mixed shows no liquid crystal properties, its amount is preferably 20 parts by weight or less, more preferably 5 parts by weight or less, per 100 parts by weight of the polymerizable liquid crystal compound of the present invention.

Specific examples of the above-mentioned specified compound include compounds represented by the following formulas (30) to (152), nematic liquid crystals, ferroelectric liquid crystals and commercially available liquid crystal compositions although not limited thereto.

[Chemical Formula 15]

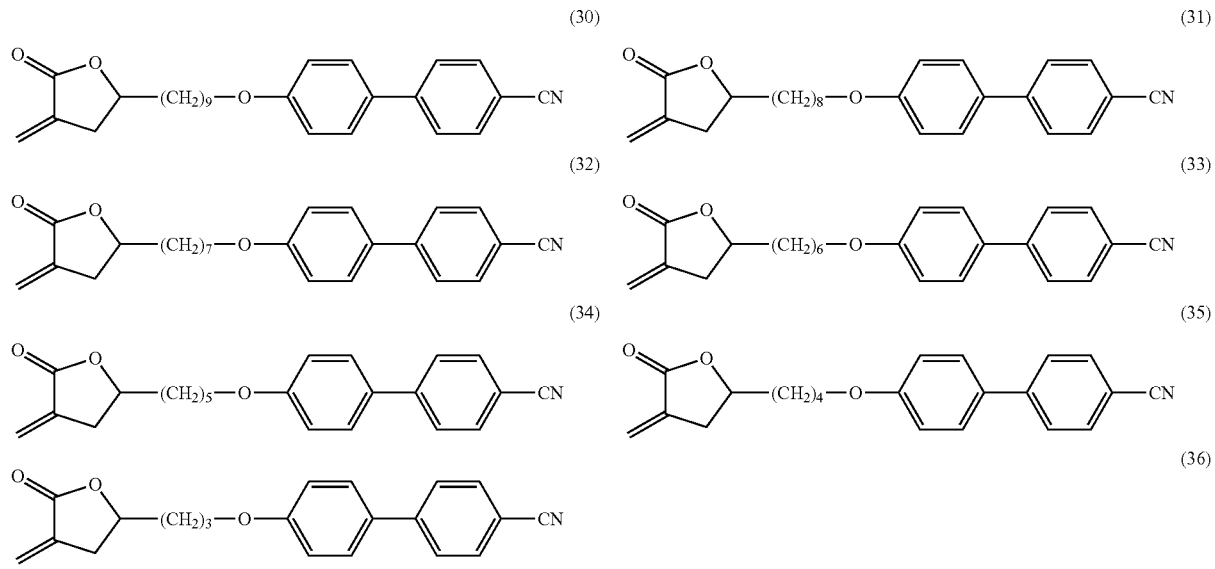

[Chemical Formula 16]

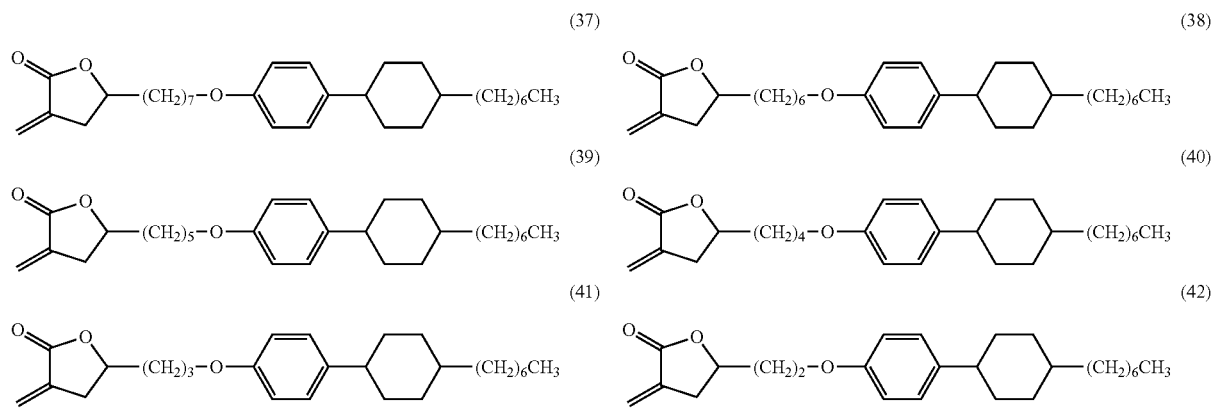

[Chemical Formula 17]

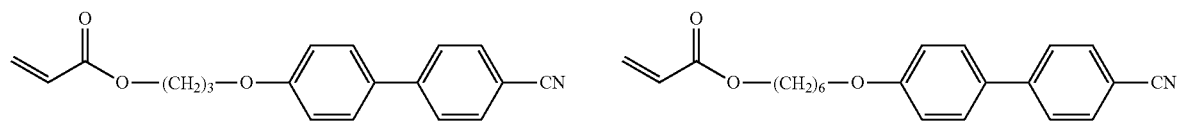

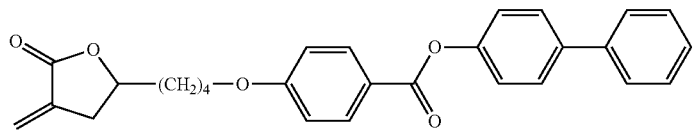
(45)
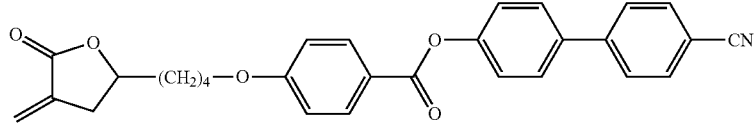
(46)
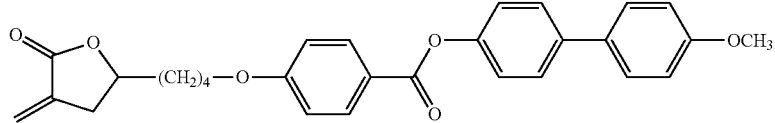
(47)
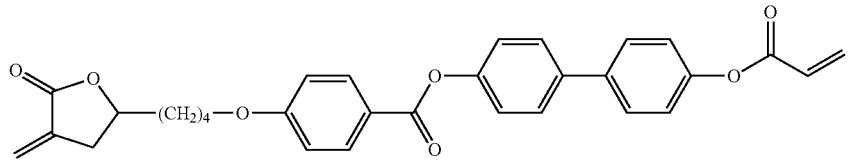
(48)
[Chemical Formula 18]
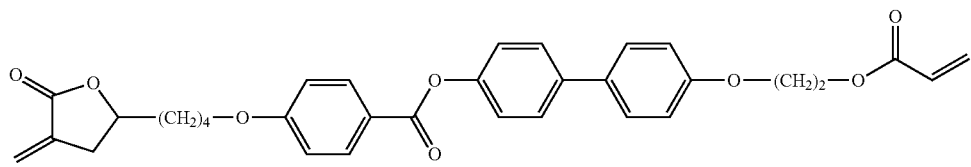
(49)
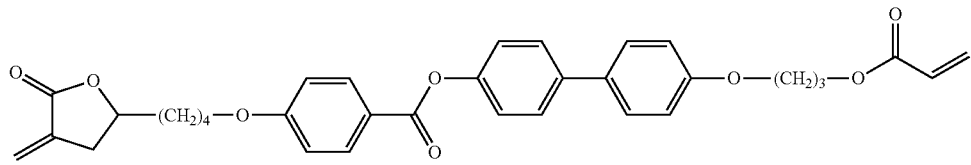
(50)
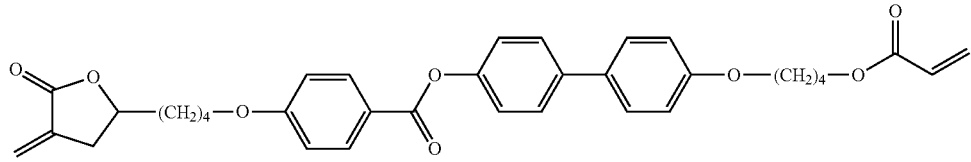
(51)
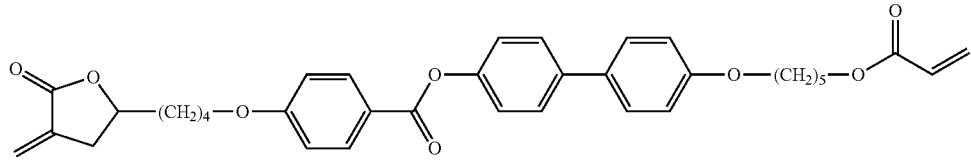
(52)
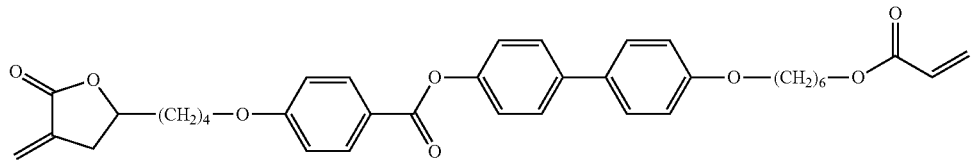
(53)

[Chemical Formula 19]
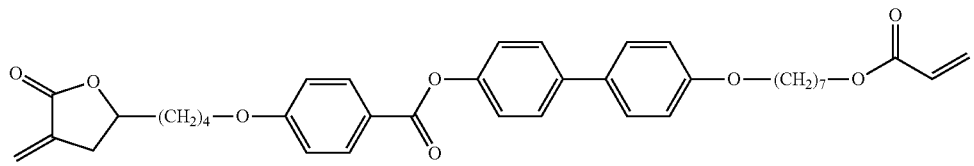 (54)
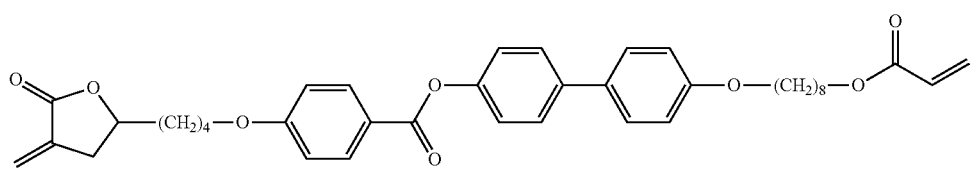 (55)
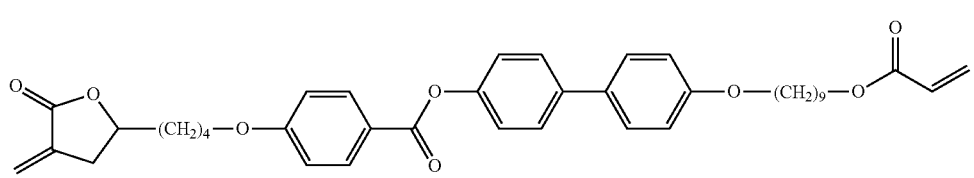 (56)
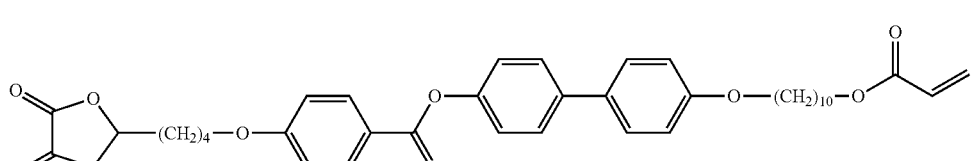 (57)
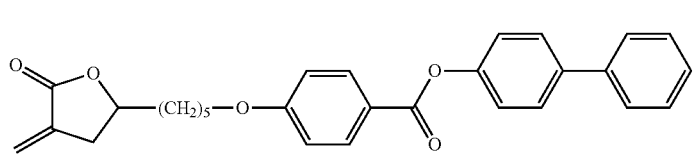 (58)
[Chemical Formula 20]
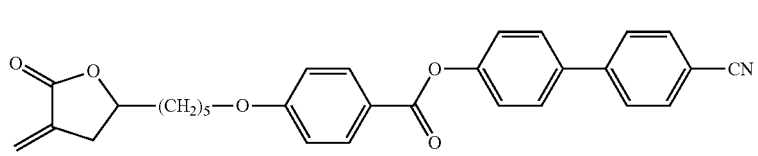 (59)
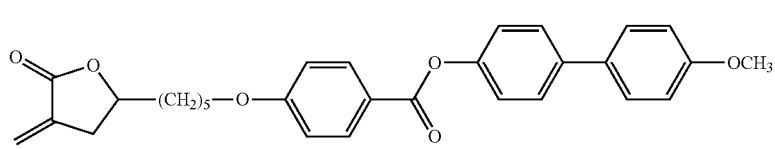 (60)
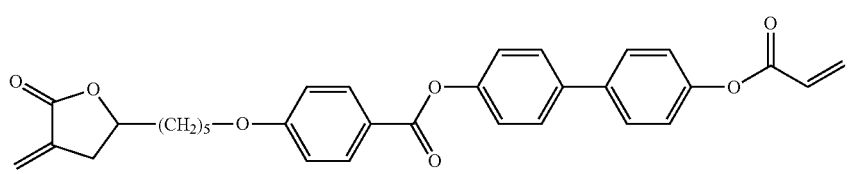 (61)
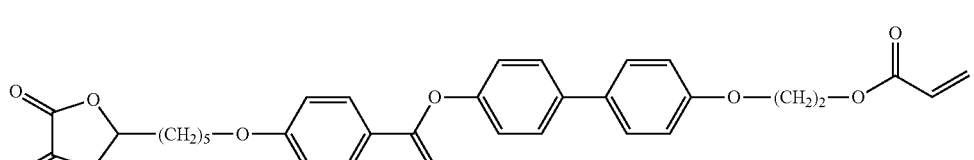 (62)

-continued
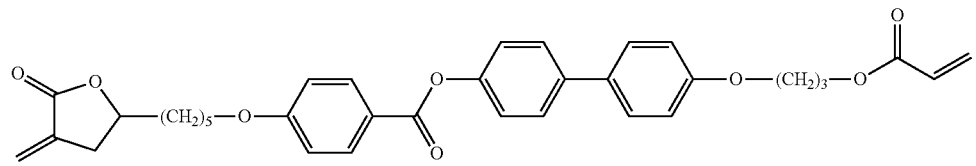
(63)
[Chemical Formula 21]
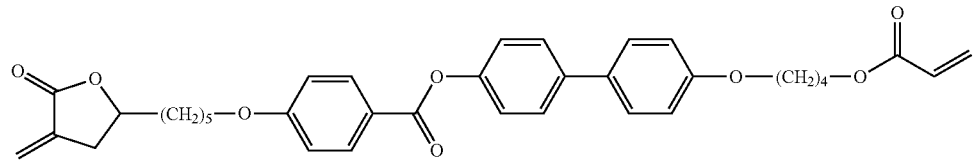
(64)
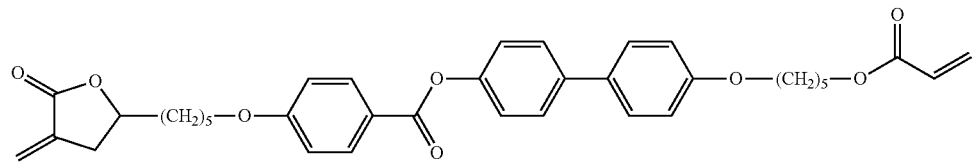
(65)
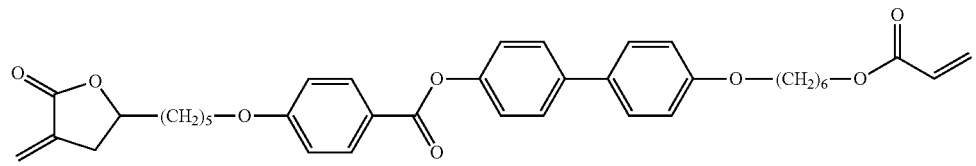
(66)
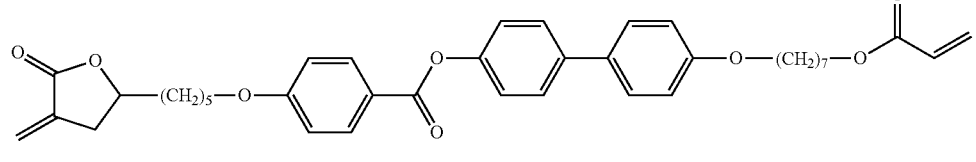
(67)
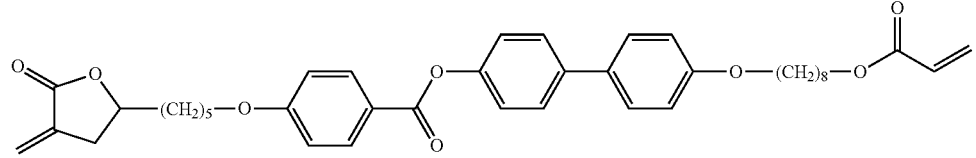
(68)
[Chemical Formula 22]
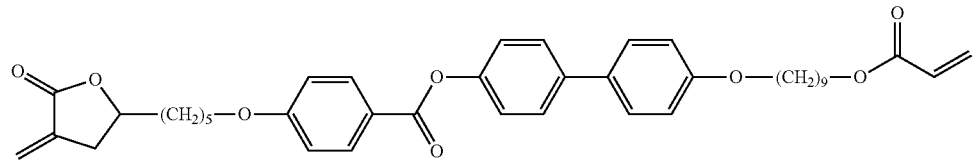
(69)
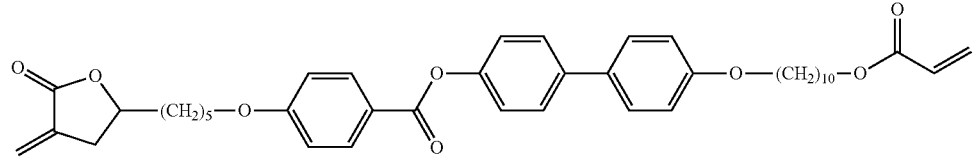
(70)
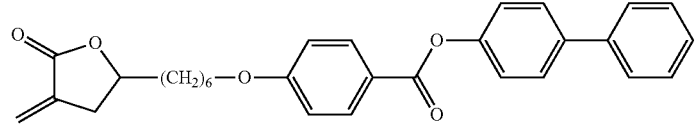
(71)

(72)
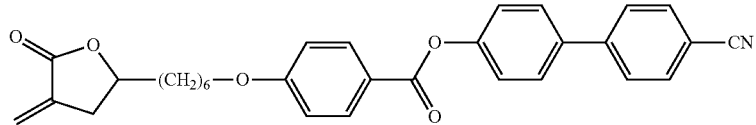
(73)
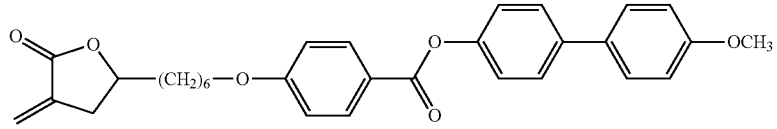
[Chemical Formula 23]
(74)
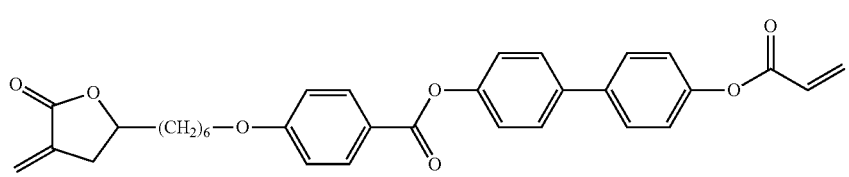
(75)
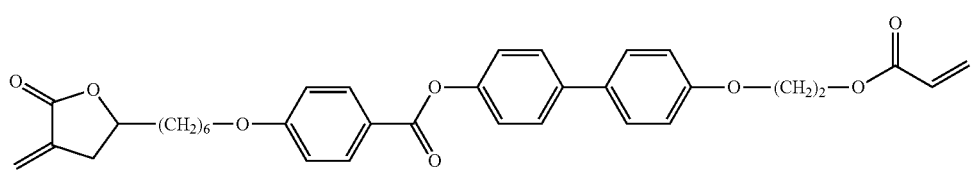
(76)
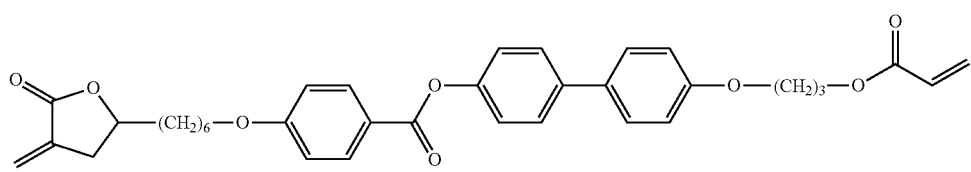
(77)
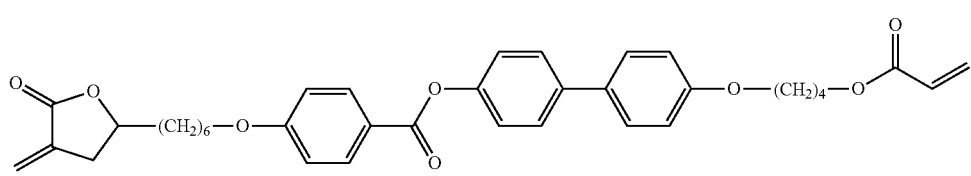
(78)
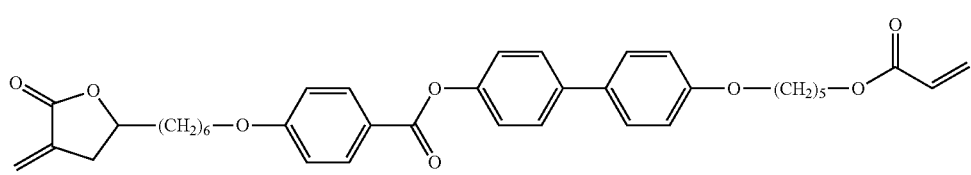
[Chemical Formula 24]
(79)
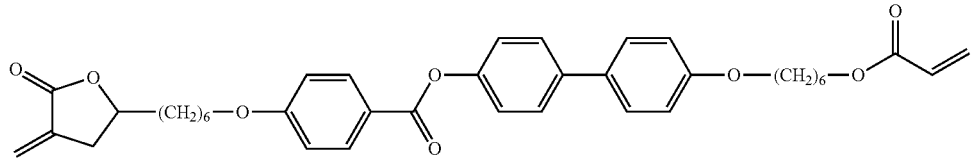
(80)
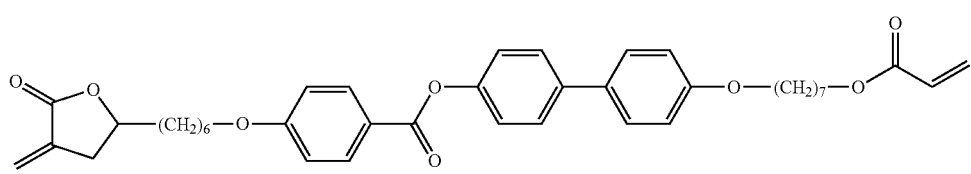

-continued
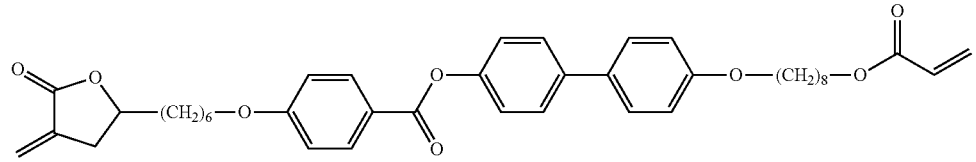
(81)
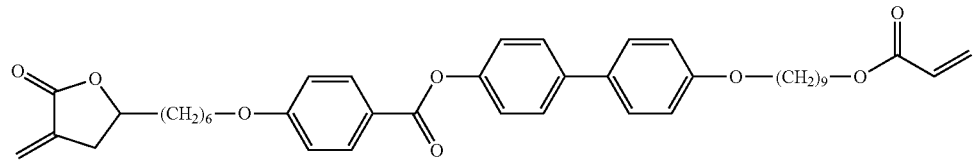
(82)
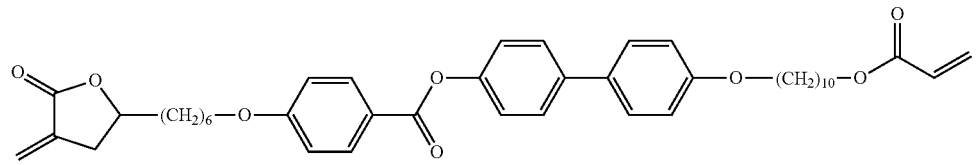
(83)
[Chemical Formula 25]
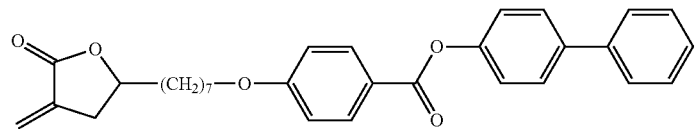
(84)
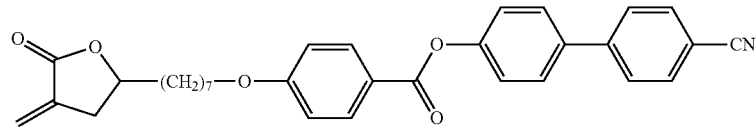
(85)
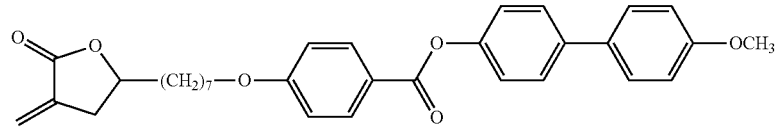
(86)
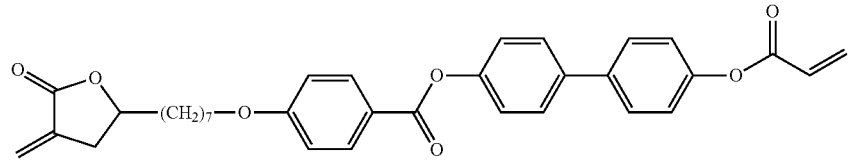
(87)
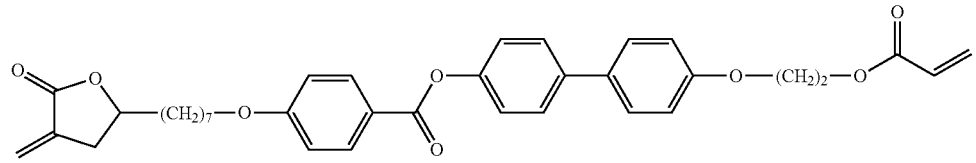
(88)
[Chemical Formula 26]
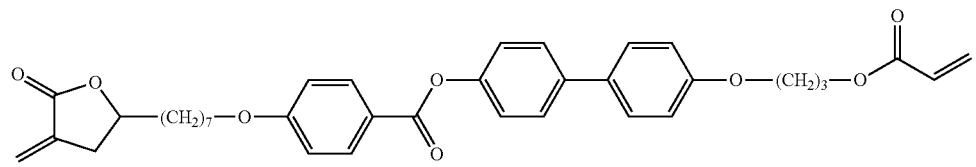
(89)

-continued
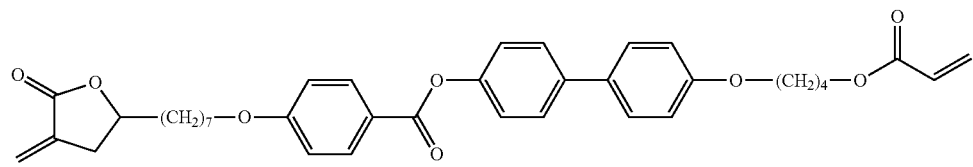
(90)
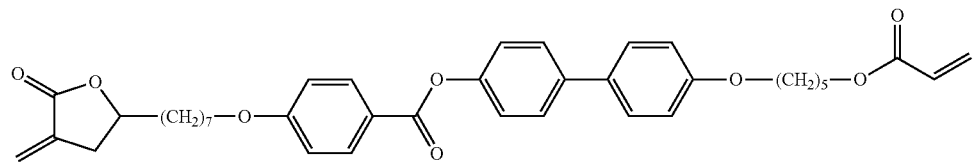
(91)
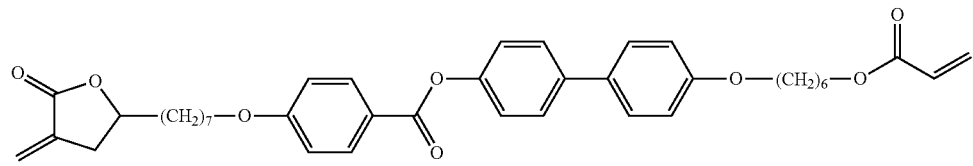
(92)
(93)
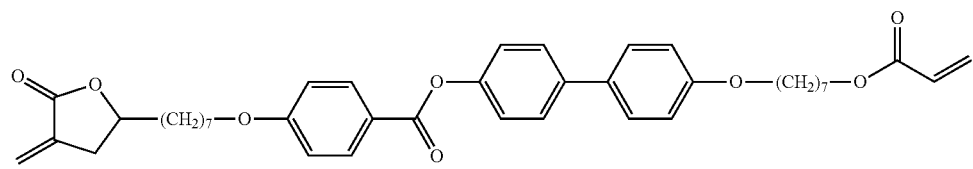
[Chemical Formula 27]
(94)
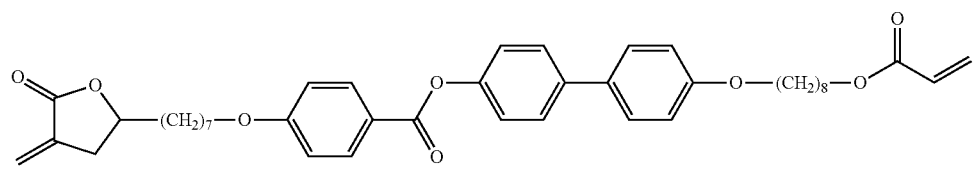
(95)
(96)
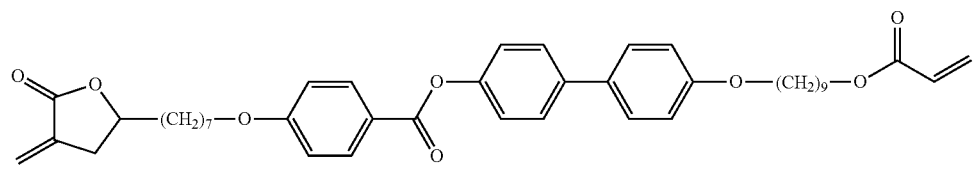
(97)
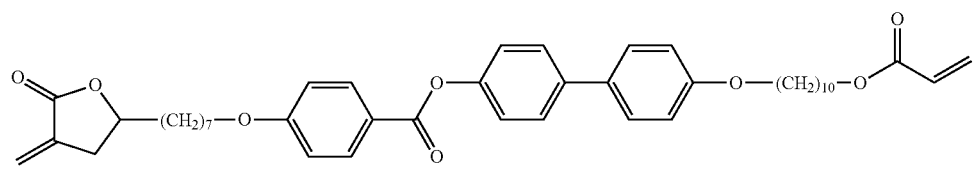
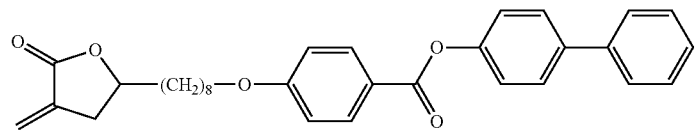
(98)
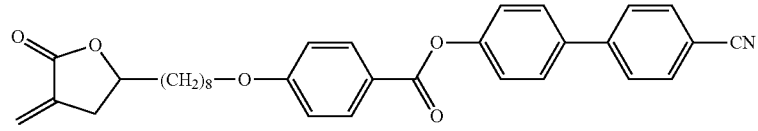

[Chemical Formula 28]
(99)
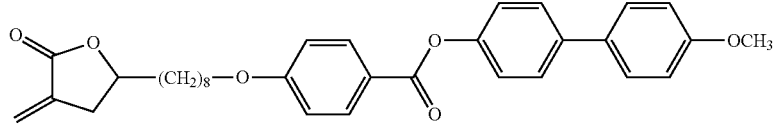
(100)
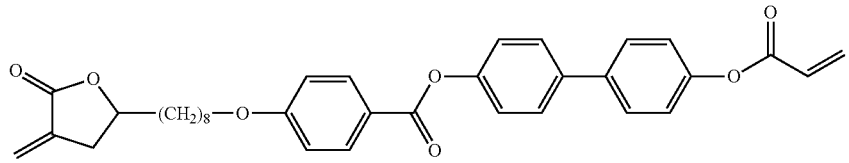
(101)
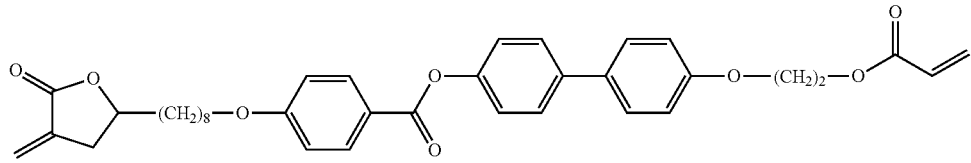
(102)
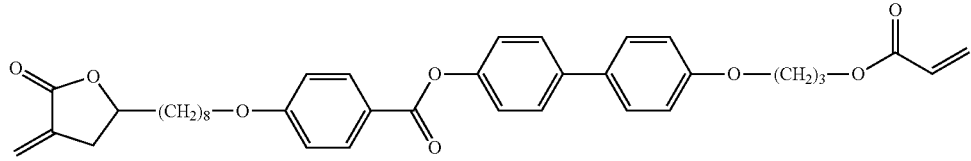
(103)
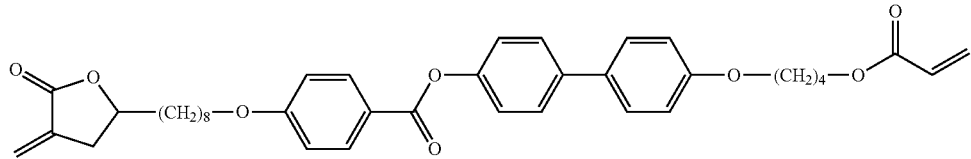
[Chemical Formula 29]
(104)
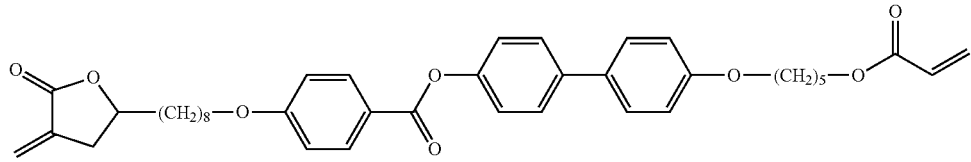
(105)
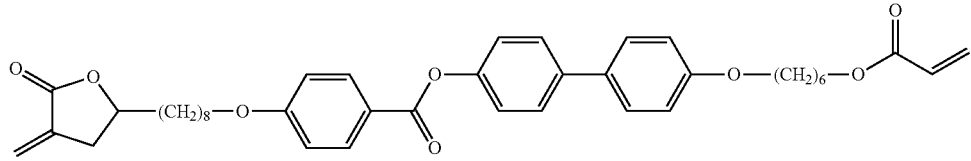
(106)
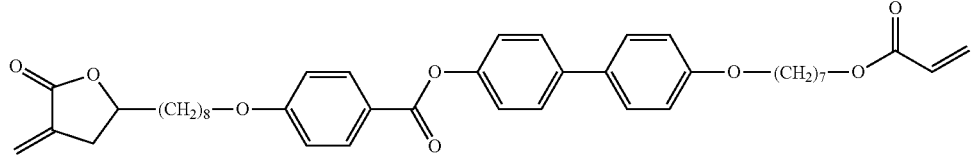
(107)
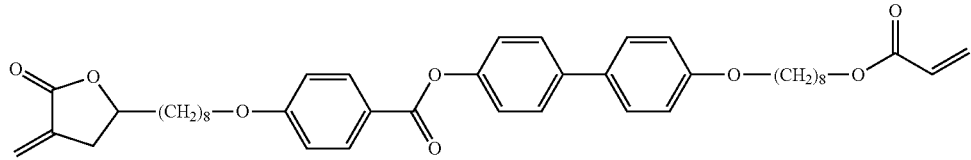

-continued
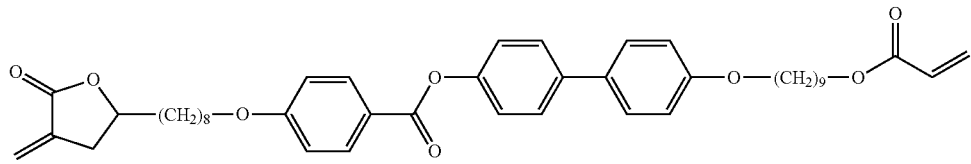
(108)
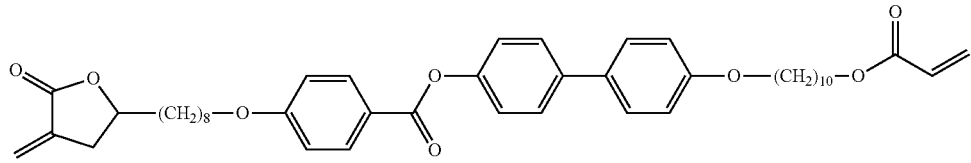
(109)
[Chemical Formula 30]
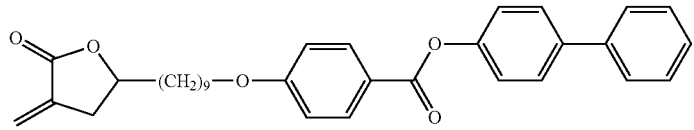
(110)
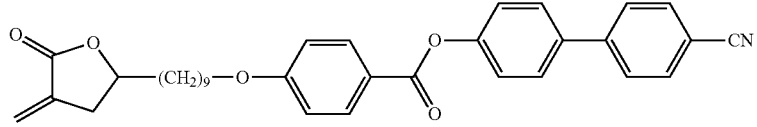
(111)
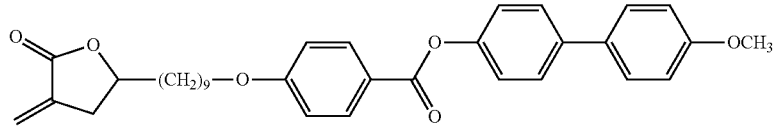
(112)
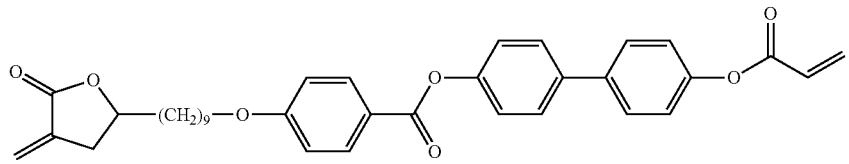
(113)
[Chemical Formula 31]
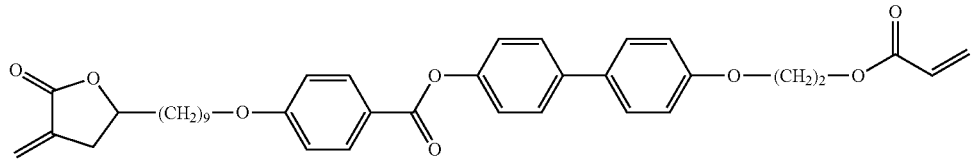
(114)
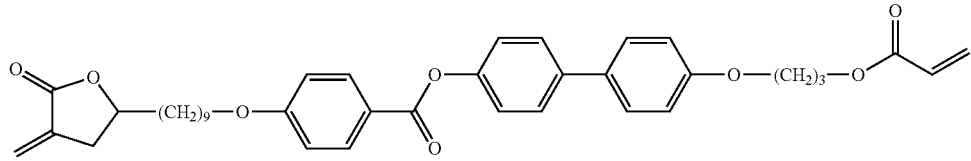
(115)
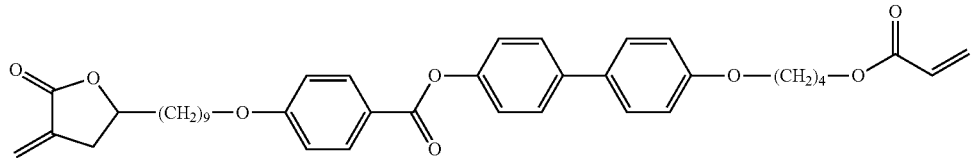
(116)

-continued
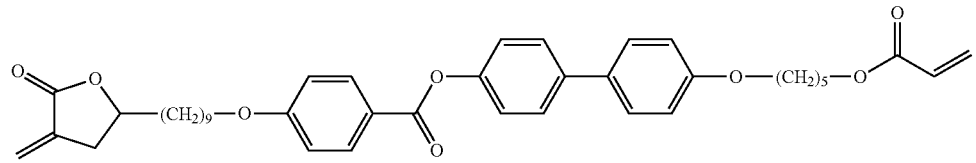
(117)
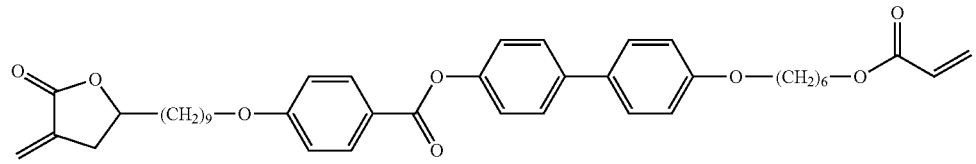
(118)
[Chemical Formula 32]
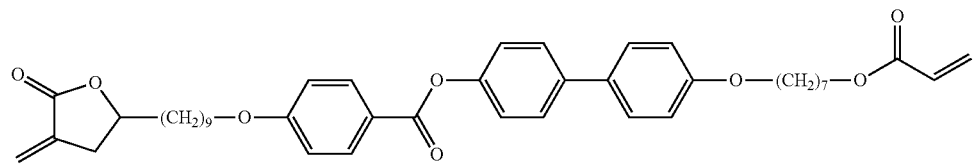
(119)
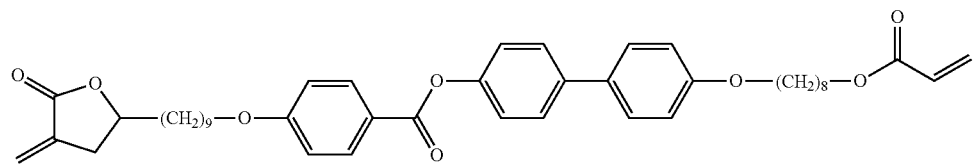
(120)
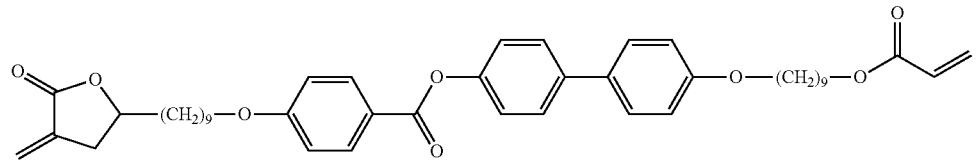
(121)
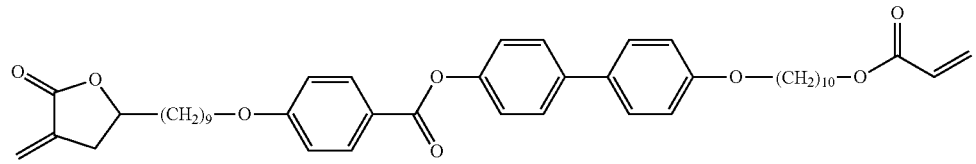
(122)
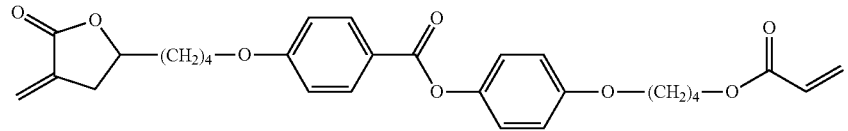
(123)
[Chemical Formula 33]
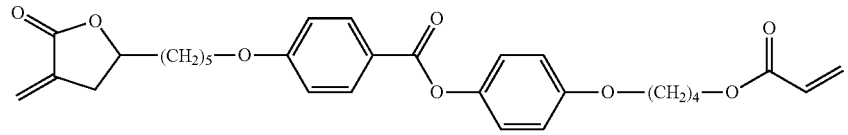
(124)
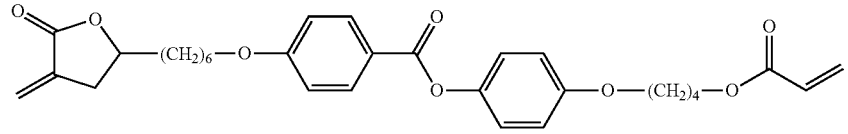
(125)

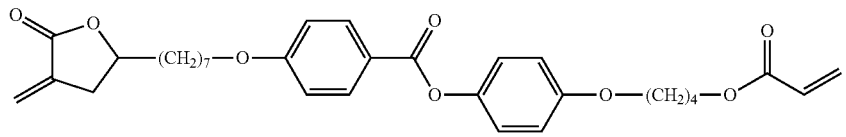
(126)
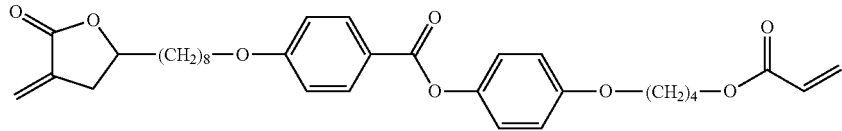
(127)
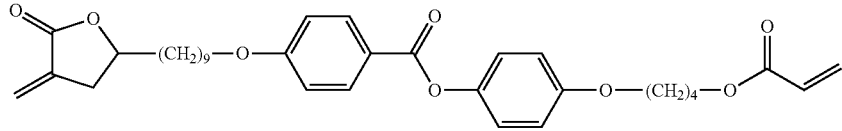
(128)
[Chemical Formula 34]
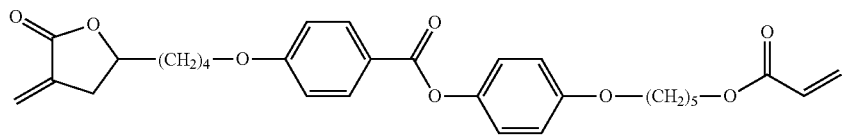
(129)
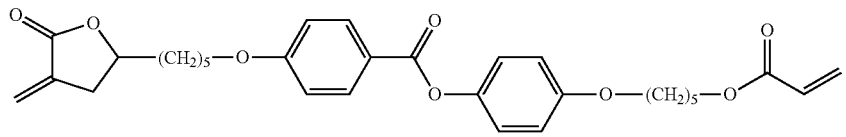
(130)
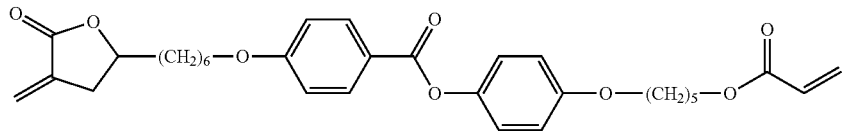
(131)
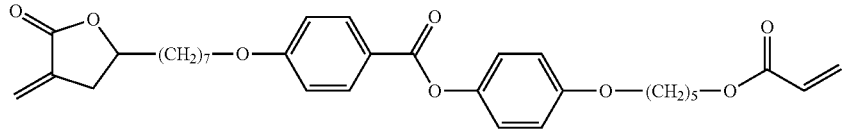
(132)
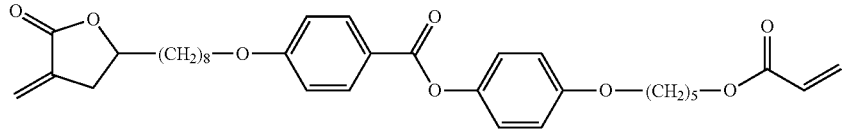
(133)
[Chemical Formula 35]
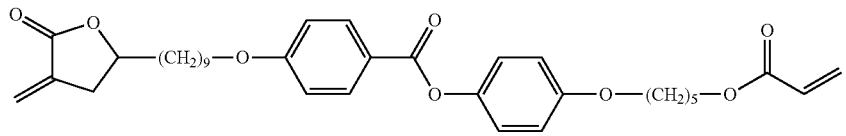
(134)
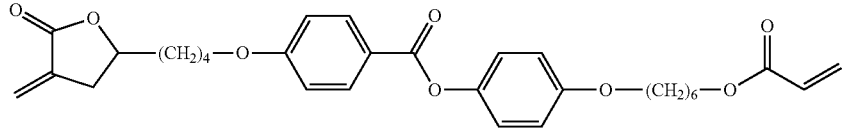
(135)

-continued
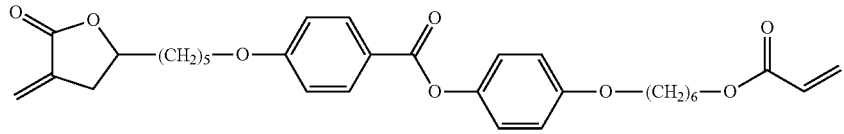 (136)
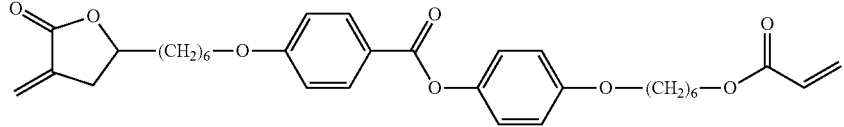 (137)
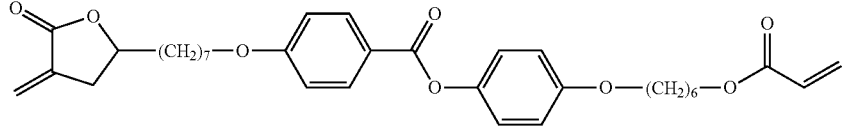 (138)
[Chemical Formula 36]
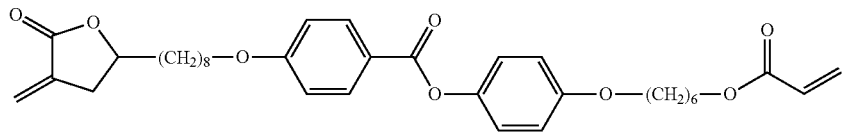 (139)
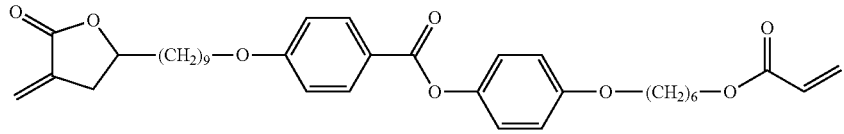 (140)
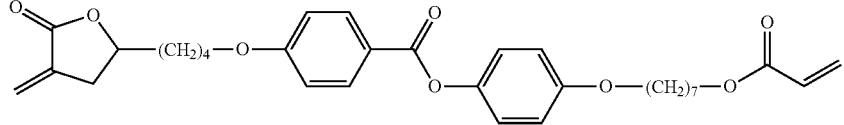 (141)
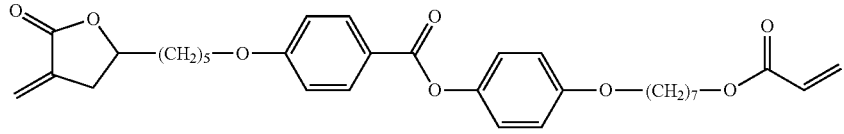 (142)
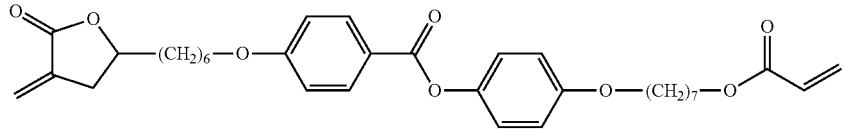 (143)
[Chemical Formula 37]
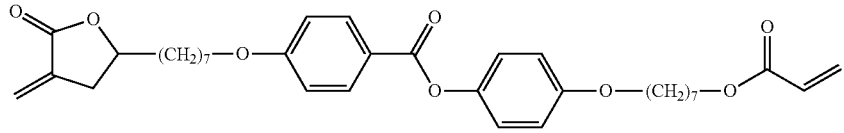 (144)
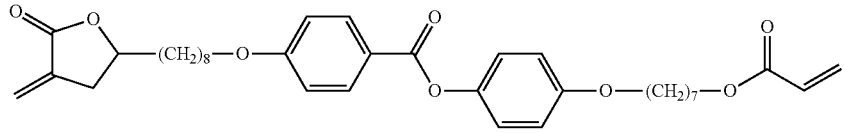 (145)

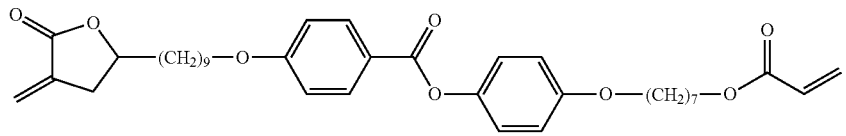

(146)

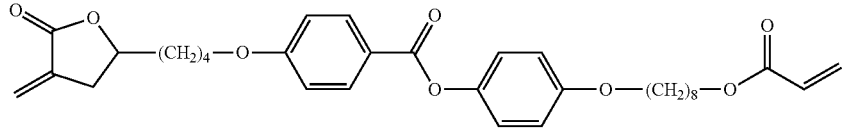

(147)

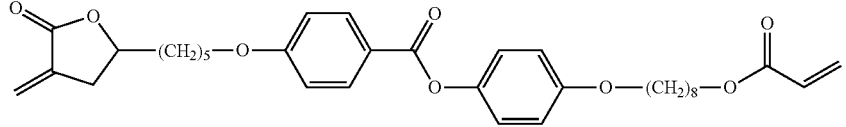

(148)

[Chemical Formula 38]

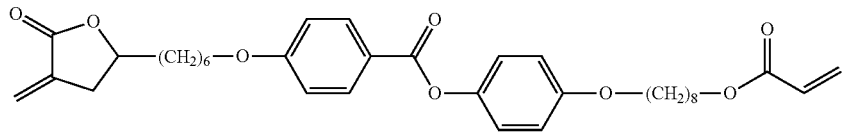

(149)

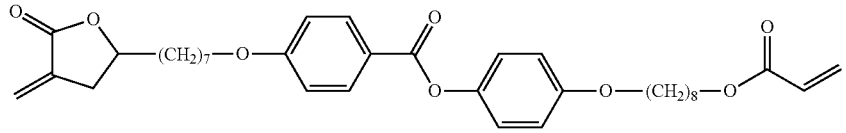

(150)

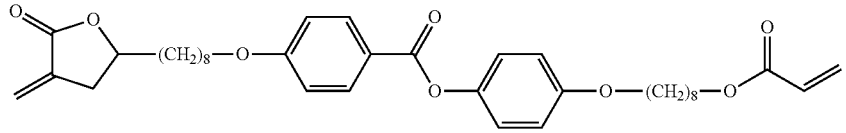

(151)

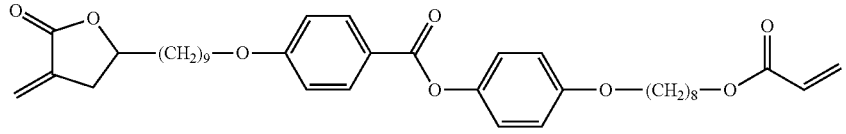

(152)

For the purpose of improving polymerization reactivity, a photopolymerization initiator, thermal polymerization initiator or photosensitizer may be added to the polymerizable liquid crystal composition of the present invention.

As a photopolymerization initiator, mention is made, for example, of benzoin ethers such as benzoin methyl ether, benzophenones such as benzophenone, acetophenones such as diethoxyacetophenone, benzyl ketals such as benzyl dimethyl ketal and the like. Such photopolymerization initiators may be used in combination of a plurality thereof.

The amount of the photopolymerization initiator is preferably 5 parts by weight or less, more preferably 0.5 to 2 parts by weight, per 100 parts by weight of the total of polymerizable liquid crystal compounds represented by the formula [1] or the total of a polymerizable liquid crystal compound represented by the formula [1] and a specified compound having a polymerizable group and showing liquid crystal properties (a combination of both hereinafter referred to as total polymerizable liquid crystal compounds).

The thermal polymerization initiators include, for example, 2,2'-azobisisobutyronitrile and the like. The thermal polymerization initiators may be used in combination of a plurality thereof. The amount is preferably 5 parts by weight or less, more preferably 0.5 to 2.0 parts by weight, per 100 parts by weight of the total polymerizable liquid crystal compounds.

The photosensitizers include, for example, anthracene photosensitizers such as anthracene and the like. The photosensitizers may be used in combination of a plurality thereof. The amount is preferably 5 parts by weight or less per 100 parts by weight of the total polymerizable liquid crystal compounds.

It will be noted that the above-mentioned photopolymerization initiator may be used in combination with at least one of the thermal polymerization initiator and the photosensitizer.

The polymerizable liquid crystal composition of the present invention may be admixed with a stabilizer so as to improve storage stability.

The stabilizers include, for example, hydroquinone, a hydroquinone monoalkyl ether such as hydroquinone monomethyl ether, and 4-t-butylcatechol and the like. The stabilizer may be used in combination of a plurality thereof. The amount is 0.1 part by weight or less per 100 parts by weight of the total polymerizable liquid crystal compounds.

In order to improve adhesion to a substrate, adhesion promoters may be added to the polymerizable liquid crystal composition of the present invention.

As an adhesion promoter, mention is made of: chlorosilanes such as trimethylchlorosilane, dimethylvinylchlorosilane, methyldiphenylchlorosilane, chloromethyldimethylchlorosilane and the like; alkoxysilanes such as trimethylmethoxysilane, dimethyldiethoxysilane, methyldimethoxysilane, dimethylvinylethoxysilane, diphenyldimethoxysilane, phenyltriethoxysilane and the like; silazanes such as hexamethyldisilazane, N,N'-bis(trimethylsilyl) urea, dimethyltrimethylsilylamine, trimethylsilylimidazole and the like; silanes such as vinyltrichlorosilane, γ-chloropropyltrimethoxysilane, γ-aminopropyltriethoxysilane, γ-methacryloxypropyltrimethoxysilane, γ-glycidoxypropyltrimethoxysilane, γ-(N-piperidinyl)propyltrimethoxysilane and the like; heterocyclic compounds such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, mercaptopyrimidine and the like; urea compounds such as 1,1-dimethylurea, 1,3-dimethylurea and the like; and thiourea compounds.

The adhesion promoters may be used in combination of a plurality thereof, and the amount is preferably not larger than 1 part by weight or less per 100 parts by weight of the total polymerizable liquid crystal compounds.

The polymerizable liquid crystal composition of the present invention may be admixed with an organic solvent so as to adjust a viscosity thereof. In this case, the composition may not be allowed to show liquid crystal properties in the state of an organic solvent being contained.

As an organic solvent, mention is made, for example, of: ethers such as tetrahydrofuran, dioxane and the like; aromatic hydrocarbons such as benzene, toluene, xylene and the like; polar solvents such as N,N-dimethylformamide, N-methyl-2-pyrrolidone and the like; esters such as ethyl acetate, butyl acetate, ethyl lactate and the like; alkoxy esters such as methyl 3-methoxypropionate, methyl 2-methoxypropionate, ethyl 3-methoxypropionate, ethyl 2-methoxypropionate, ethyl 3-ethoxypropionate, ethyl 2-ethoxypropionate and the like; glycol dialkyl ethers such as ethylene glycol dimethyl ether, propylene glycol dimethyl ether and the like; diglycol dialkyl ethers such as diethylene glycol dimethyl ether, diethylene glycol diethyl ether, diethylene glycol methylethyl ether, dipropylene glycol dimethyl ether and the like; glycol monoalkyl ethers such as ethylene glycol monomethyl ether, ethylene glycol monoethyl ether, propylene glycol monomethyl ether, propylene glycol monoethyl ether and the like; diglycol monoalkyl ethers such as diethylene glycol monomethyl ether, diethylene glycol monoethyl ether, dipropylene glycol monomethyl ether, dipropylene glycol monoethyl ether, and the like; glycol monoalkyl ether esters such as propylene glycol monomethyl ether acetate, carbitol acetate, ethyl cellosolve acetate and the like; and ketones such as cyclohexanone, methyl ethyl ketone, methyl isobutyl ketone, 2-heptanone and the like. These organic solvents may be used singly or in combination of at least two.

Of these, it is preferred from the standpoints of safety for global environment and working environment to use propylene glycol monomethyl ether, propylene glycol monomethyl ether acetate and ethyl lactate.

It will be noted that the amount of the solvent is preferably at about 60 to 95 wt % in the polymerizable liquid crystal composition.

For the purpose of improving affinity for a substrate, surfactants may be added to the polymerizable liquid crystal composition of the present invention. The surfactant is not critical in type and includes a fluorine-based surfactant, a silicone-based surfactant, a nonionic surfactant and the like. The fluorine-based surfactant that has a high effect of improving substrate affinity is preferred.

Specific examples of the fluorine-based surfactant (commercial names indicated hereinbelow) include F-Top EF301, EF303, EF352 (made by K.K. Tochem Products), Megafac F171, F173, R-30 (made by DIC Corporation), Florad FC430, FC431 (made by Sumitomo 3M, Limited), Asahiguard AG710, Surflon S-382, SC101. SC102, SC103, SC104, SC105, SC106 (made by ASAHI GLASS CO., LTD.), and the like although not limited thereto. It will be noted that the surfactants may be used in combination of a plurality thereof.

As a preferred example of the polymerizable liquid crystal composition of the present invention, mention is made of a liquid crystal composition including 100 parts by weight of a polymerizable liquid crystal compound represented by the formula [1], 20 parts by weight or less of a specified compound showing no liquid crystal properties, and 5 parts by weight or less of a photopolymerization initiator, and a liquid crystal composition including 100 parts by weight of a polymerizable liquid crystal compound represented by the formula [1], 200 to 15 parts by weight of a specified compound showing liquid crystal properties, and 5 parts by weight or less of a photopolymerization initiator although not limited thereto.

The polymerizable liquid crystal composition illustrated above can be conveniently utilized as a composition or a coating solution for the formation of an orientation film.

The method of preparing the polymerizable liquid crystal composition of the present invention is not critical.

The respective ingredients for the polymerizable liquid crystal composition may be mixed at one time or may be mixed in order. When mixed in order, the order of addition of the respective ingredients are arbitrary.

It will be noted that where a plurality of compounds are used for one ingredient, a mixture obtained by previously mixing the compounds may be mixed with other ingredients, or individual compounds may be separately mixed with other ingredients.

The polymerizable liquid crystal composition of the present invention should preferably exhibit a stable liquid crystalline phase at room temperature (20-40° C. herein and whenever it appears hereinafter) so as to prevent unintentional thermal polymerization from occurring in the photopolymerization in a liquid crystal state upon preparation of an optical anisotropic body thereby permitting the molecules to be readily fixed in a uniformly oriented state. Where an organic solvent is contained in the polymerizable liquid crystal composition, a stable liquid crystalline phase should preferably be shown upon removal of the solvent.

[Polymer and Film]

The polymerizable liquid crystal of the present invention set out above are subjected to light irradiation or thermal treatment to obtain a polymer.

Further, there can be obtained a film when the polymerizable liquid crystal composition is sandwiched between two substrates or is coated onto a substrate according to a spin coating or casting method, followed by light irradiation.

The substrates used include glass, quartz, a color filter, a plastic sheet or film such as of triacetyl cellulose (TAC) and the like. It is to be noted that if two substrates are used, one of the substrates may be glass, a plastic sheet, a plastic film or a stainless steel, on which a functional thin film such as ITO or the like has been formed, or a belt or drum plated or vacuum-deposited with chromium or aluminum.

For the purpose of improving orientation properties of the resultant film, it is preferred to subject an employed substrate to orientation treatment. For the orientation treatment, there can be appropriately selected and used known methods including an orientation method wherein an orienting material containing a polyimide precursor, a polyimide, polyvinyl cinnamate or the like is coated and subjected to orientation treatment by rubbing or irradiation of polarized UV light, a method of forming an obliquely evaporated film of silicon dioxide, a method of forming a Langmuir film, and the like.

With a method of sandwiching the polymerizable liquid crystal composition between two substrates, a cell is formed by forming a gap between the two substrates by use of spacers, and the polymerizable liquid crystal composition is charged into the cell by a procedure of utilizing the capillary action or by a method wherein the gap in the cell is reduced in pressure, followed by irradiation with light for polymerization.

According to a simpler procedure, mention may be made of a method wherein a polymerizable liquid crystal composition is placed on a substrate on which spacers are disposed, on which another substrate is further placed to provide a cell, followed by polymerization by irradiation with light.

On this occasion, although the polymerizable liquid crystal composition may be one that is fluidized or may be fluidized by heating or the like after placing on a substrate, the polymerizable liquid crystal composition should be fluidized prior to superposition of another substrate.

The method of coating the polymerizable liquid crystal composition includes the step of coating the polymerizable liquid crystal composition and may further include the step of heating such as with a hot plate, if necessary, during the course of the polymerization step by application of light or heat. When using a polymerizable liquid crystal composition containing an organic solvent, this step is especially effective as a measure for removing the organic solvent from the composition.

In any of the above methods, there can be obtained an oriented film having optical anisotropy by polymerizing the polymerizable liquid crystal composition under conditions where it exhibits a liquid crystalline phase.

In order to obtain a polymer of the multi-domain state where adjacent domains, respectively, have different orientations, there are used a method of establishing multi-domain alignment in a polymerization process or a method of allowing the orientation treatment of a substrate to establish multi-domains alignment.

The method of establishing multi-domain alignment by a polymerization process includes a method wherein UV light is irradiated onto a polymerizable liquid crystal composition in liquid crystal state through a mask to form polymerized domains and the other domains are polymerized in an isotropic liquid state.

For the method of allowing the orientation treatment of a substrate to establish multi-domain alignment, mention is made of a method of rubbing an orienting material formed on a substrate through a mask, a method of irradiating UV light through a mask, and the like.

According to these methods, there can be obtained a substrate, subjected to multi-domain alignment, wherein rubbed domains and UV-irradiated domains are oriented portions, and the others are non-treated portions. The polymerizable liquid crystal composition formed on the substrate subjected to multi-domain alignment undergoes multi-domain conversion by the influence of the oriented material layer.

It will be noted that aside from the above orientation methods, there may be used methods using an electric field and a magnetic field, respectively.

When using the polymerizable liquid crystal composition of the present invention, there can be obtained a film having optical anisotropy, for which it can be conveniently employed as a polarizer, a wave plate and the like. Additionally, such a film exhibits a high chemical resistance and has an advantage in that when a pattern is formed in air by use of photolithography, a film loss in a developing step is small.

EXAMPLES

The present invention is more particularly described by way of Synthetic Examples, Examples and Comparative Examples, and the present invention should not be construed as limited to the following Examples. It will be noted that measuring methods and measuring conditions of the respective physical properties in the Examples are as described below.

[1] NMR

A compound was dissolved in deuterochloroform ($CDCl_3$) or deutero dimethylsulfoxide (DMSO-d6) and $^1$H-NMR at 300 MHz was measured by use of a nuclear magnetic resonator (made by Diol Co., Ltd.).

[2] Observation of Liquid Crystalline Phase

Liquid crystalline phase was identified in such a way that a sample was heated on a hot stage (MATS-2002S, made by Tokai Hit Co., Ltd.), followed by observation through a polarization microscope (made by Nikon Corporation). The phase transition temperature was measured under conditions of a scanning speed (Scan Rate) of 10° C./minute by use of a differential scanning calorimeteric analyzer (DSC3100SR), made by Mac Science Co., Ltd.

[3] Haze Value

The haze value of a film was measured by use of Spectral Haze Meter (TC-1800H), made by Tokyo Denshoku Co. Ltd.

[4] Retardation Value of Film

A retardation value at a wavelength of 590 nm was measured by use of a retardation measuring apparatus (RETS-100, made by Otsuka Electronics Co., Ltd.).

[1] Polymerizable Liquid Crystal Composition

Synthetic Example 1

Synthesis of Polymerizable Liquid Crystal Compound (E1)

[Chemical Formula 39]

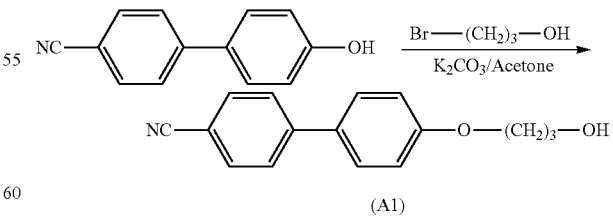

9.8 g (50.0 mmol) of 4-cyano-4'-hydroxybiphenyl, 7.0 g (50.0 mmol) of 3-bromo-1-propanol, 13.8 g of potassium carbonate (100 mmol) and 150 ml of acetone were added to a 500-ml round-bottomed flask equipped with a condenser tube to provide a mixture, followed by reaction under agitation at 64° C. for 48 hours. After completion of the reaction, the solvent was distilled off under reduced pressure to obtain a yellow wet solid. Thereafter, this solid and 140 ml of water were mixed together, to which 100 ml of diethyl ether was added for extraction. The extraction was repeated three times. The separated organic phase was dried by addition of anhydrous magnesium sulfate and filtered, followed by distilling off the solvent under reduced pressure to obtain a yellow solid. This solid was purified by re-crystallization from a mixed solvent of hexane/ethyl acetate=2/1 to obtain 8.7 g of a white solid. The results of NMR measurement of the solid are indicated below. From the results, it was confirmed that this white solid was an intermediate compound (A1) (yield: 70%)

$^1$H-NMR (CDCl$_3$) δ: 2.09 (m, 2H), 3.90 (t, 2H), 4.20 (t, 2H), 6.99 (d, 2H), 7.52 (d, 2H), 7.66 (m, 4H).

[Chemical Formula 40]

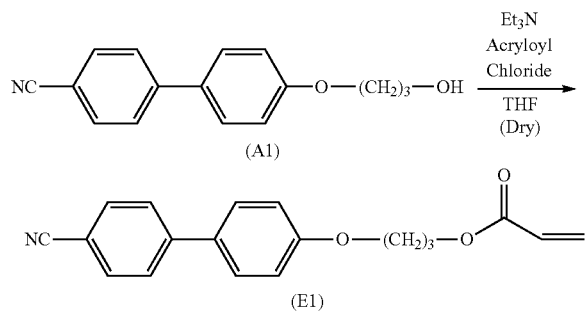

12.0 g of the thus obtained intermediate compound (A1) was dissolved in 40 ml of tetrahydrofuran (THF) along with 7.7 ml of triethylamine and a small amount of BHT (2,6-di-tert-butyl-p-cresol) and agitated at room temperature, in which a solution of 4.6 ml of acryloyl chloride in 40 ml of THF was dropped for 15 minutes under cooling on a water bath. After the dropping, the solution was agitated for 30 minutes, and the agitation was continued overnight while returning to room temperature after removal of the water bath, followed by filtering precipitated TEA hydrochloride salt. About ¾ of the THF was distilled off from the resulting filtrate, to which 50 ml of methylene chloride was added, and the resulting organic phase was successively washed with 50 ml of a saturated sodium hydrogen carbonate, 50 ml of 0.5-N HCl and 50 ml of a saturated saline solution, followed by drying with magnesium sulfate and removing the solvent by distillation to obtain a product. After recrystallization from ethanol, 6.0 g of compound (E1) was obtained.

$^1$H-NMR (CDCl$_3$) δ: 2.20 (m, 2H), 4.10 (t, 2H), 4.40 (t, 2H), 5.81 (d, 1H), 6.15 (m, 1H), 6.41 (d, 1H), 6.99 (d, 2H), 7.55 (d, 2H), 7.66 (m, 4H).

Synthetic Example 2

Synthesis of Polymerizable Liquid Crystal Compound (E2)

[Chemical Formula 41]

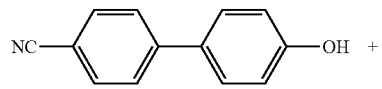

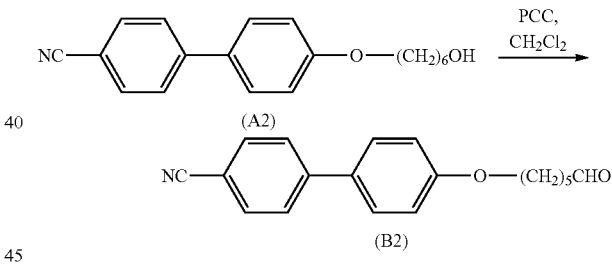

5.0 g (25.6 mmol) of 4-cyano-4'-hydroxybiphenyl, 4.6 g (25.6 mmol) of 6-bromo-1-hexanol, 7.0 g (50 mmol) of potassium carbonate and 50 ml of acetone were added to a 100-ml round-bottomed flask equipped with a condenser tube to provide a mixture, followed by reaction under agitation at 64° C. for 24 hours. After completion of the reaction, the solvent was distilled off under reduced pressure to obtain a yellow wet solid. Thereafter, this solid and 70 ml of water were mixed together, to which 50 ml of diethyl ether was added for extraction. The extraction was repeated three times.

The separated organic phase was dried by addition of anhydrous magnesium sulfate and filtered, followed by distilling off the solvent under reduced pressure to obtain a yellow solid. This solid was dissolved in 3 ml of ethyl acetate and purified according to silica gel column chromatography (column: silica gel 60, 0.063 to 0.200 mm, made by Merck KGaA, eluate: hexane/ethyl acetate=1/1). The solvent was distilled off from the solution to obtain 6.9 g of a white solid. The results of NMR measurement of the solid are indicated below. From the results, it was confirmed that this white solid was an intermediate compound (A2) (yield: 91%)

$^1$H-NMR (DMSO-d6) δ: 1.26 (m, 6H), 1.69 (m, 2H), 3.37 (t, 2H), 4.03 (t, 2H), 7.06 (d, 2H), 7.69 (d, 2H), 7.85 (m, 4H).

[Chemical Formula 42]

Next, 2.2 g (10.0 mmol) of pyridinium chlorochromate (hereinafter abbreviated as PCC) and 30.0 ml of CH$_2$Cl$_2$ were added to a 200-ml three-necked flask equipped with a condenser tube, in which a solution of 2.95 g (10.0 mmol) of the intermediate compound (A2) obtained above in CH$_2$Cl$_2$ (50.0 ml) was dropped while mixing under agitation, followed by further agitation at 40° C. for 0.5 hours. Subsequently, to the solution which was separated from an oily matter attached to the walls of the flask, 90 ml of diethyl ether was added and filtered under reduced pressure, followed by distilling off the solvent under reduced pressure to obtain a dark green wet solid.

The solid was dissolved in 3 ml of ethyl acetate and purified according to silica gel column chromatography (column: silica gel 60, 0.063 to 0.200 mm, made by Merck KGaA, eluate: hexane/ethyl acetate=1/1). The solvent was distilled off from the resulting solution to obtain 2.8 g of a colorless solid. The results of NMR measurement of the solid are indicated below. From the results, it was confirmed that the colorless solid was an intermediate compound (B2) (yield: 93%).

$^1$H-NMR (CDCl$_3$) δ: 1.84 (m, 6H), 2.50 (m, 2H), 4.02 (m, 2H), 6.99 (d, 2H), 7.53 (d, 2H), 7.91 (m, 4H), 9.80 (s, 1H).

[Chemical Formula 43]

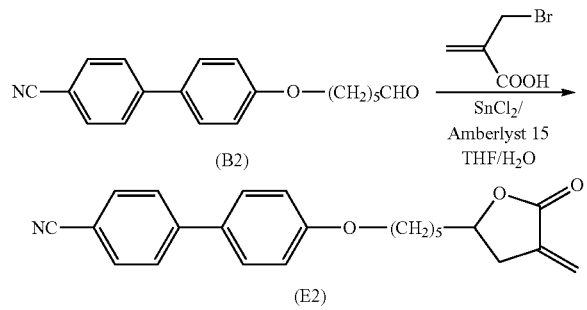

Finally, 3.0 g (10.0 mmol) of the intermediate compound (B2) obtained above, 1.65 g (10.0 mmol) of 2-(bromomethyl) acrylic acid, 1.6 g of Amberlyst (registered tradename) 15 (commercial name of Rohm and Haas Company), 16.0 ml of THF, 1.9 g (10.0 mmol) of tin (II) chloride and 4.0 ml of pure water were added to a 50-ml round-bottomed flask equipped with a condenser tube to provide a mixture, followed by reaction at 70° C. for 7 hours. After completion of the reaction, the reaction solution was filtered under reduced pressure and mixed with 30 ml of pure water, to which 50 ml of diethyl ether was added for extraction. The extraction was repeated three times.

Anhydrous magnesium sulfate was added to the organic phase obtained after the extraction for drying, and the solvent was distilled off from the solution obtained after filtration under reduced pressure to obtain a yellow solid. This solid was dissolved in 2 ml of ethyl acetate and purified according to silica gel column chromatography (column: silica gel 60, 0.063 to 0.200 mm, made by Merck KGaA, eluate: hexane/ethyl acetate=2/1). The solvent was distilled off from the resulting solution to obtain 1.5 g of a white solid. The results of NMR measurement of the solid are indicated below. From the results, it was confirmed that the white solid was an intended polymerizable liquid crystal compound (E2) (yield: 41%).

$^1$H-NMR (CDCl$_3$) δ: 1.57 (m, 6H), 1.85 (m, 2H), 2.60 (m, 1H), 3.05 (m, 1H), 4.01 (t, 2H), 4.54 (m, 1H), 5.63 (m, 1H), 6.23 (m, 1H), 7.00 (d, 2H), 7.52 (d, 2H), 7.68 (m, 4H).

It will be noted that the liquid crystal properties of the polymerizable liquid crystal compound (E2) were observed, revealing that this compound was converted to an isotropic liquid state at 84° C. and underwent phase transition to a liquid crystalline phase (nematic phase) at 61° C. when the temperature was descended.

Synthetic Example 3

Synthesis of Polymerizable Liquid Crystal Compound (E3)

[Chemical Formula 44]

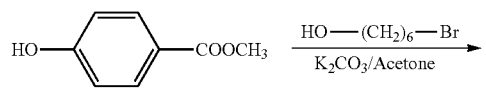

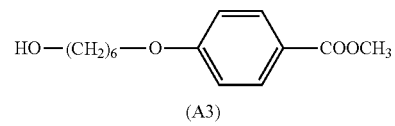

7.61 g (50.0 mmol) of methyl 4-hydroxybenzoate, 9.1 g (50.0 mmol) of 6-bromo-1-hexanol, 13.8 g (100 mmol) of potassium carbonate and 70 ml of acetone were added to a 200-ml round-bottomed flask equipped with a condenser tube to provide a mixture, followed by reaction under agitation at 64° C. for 24 hours. After completion of the reaction, the solution was filtered under reduced pressure and the solvent was distilled off under reduced pressure to obtain a yellow wet solid. Thereafter, this solid was purified by silica gel column chromatography (column: silica gel 60, 0.063 to 0.200 mm, made by Merck KGaA, eluate: hexane/ethyl acetate=1/1). The solvent was distilled off from the resulting solution to obtain 11.3 g of a white solid. The results of NMR measurement of the solid are indicated below. From the results, it was confirmed that this white solid was an intermediate compound (A3) (yield: 90%).

$^1$H-NMR (CDCl$_3$) δ: 1.3-1.7 (m, 8H), 3.67 (m, 2H), 3.88 (s, 3H), 4.03 (t, 2H), 6.91 (d, 2H), 7.99 (d, 2H).

[Chemical Formula 45]

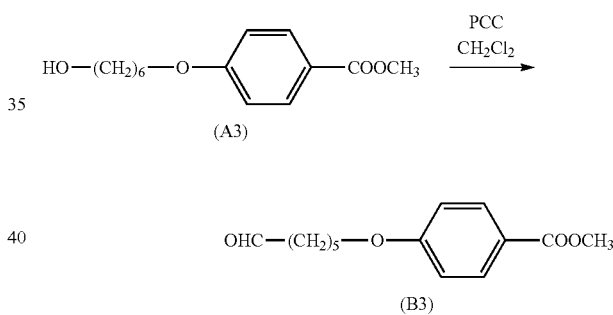

Next, 2.2 g (10.0 mmol) of PCC and 15.0 ml of CH$_2$Cl$_2$ were added to a 100-ml three-necked flask equipped with a condenser tube, in which a solution of 2.5 g (10.0 mmol) of the intermediate compound (A3) obtained above in CH$_2$Cl$_2$ (15.0 ml) was dropped while mixing under agitation, followed by further agitation at room temperature for 6 hours. Subsequently, to the solution which was separated from an oily matter attached to the walls of the flask, 90 ml of diethyl ether was added and filtered under reduced pressure, followed by distilling off the solvent under reduced pressure to obtain a dark green wet solid.

This solid was purified by silica gel chromatography (column: silica gel 60, 0.063 to 0.200 mm, made by Merck KGaA, eluate: hexane/ethyl acetate=2/1). The solvent was distilled off from the resulting solution to obtain 1.3 g of a colorless solid. The results of NMR measurement of the solid are indicated below. From the results, it was confirmed that the colorless solid was an intermediate compound (B3) (yield: 50%).

$^1$H-NMR (CDCl$_3$) δ: 1.3-1.8 (m, 6H), 2.49 (t, 2H), 3.88 (s, 3H), 3.99 (t, 2H), 6.87 (d, 2H), 7.99 (d, 2H), 9.78 (s, 1H).

[Chemical Formula 46]

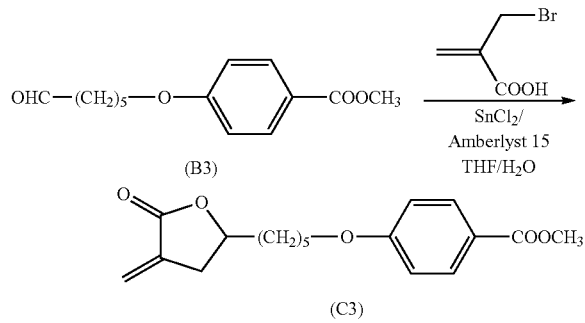

[Chemical Formula 47]

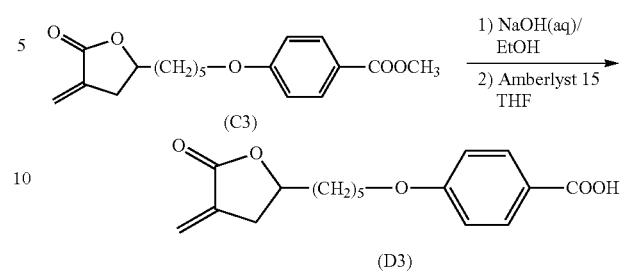

Next, 1.25 g (5.0 mmol) of the intermediate compound (B3) obtained above, 0.83 g (5.0 mmol) of 2-(bromomethyl) acrylic acid, 0.8 g of Amberlyst (registered tradename) 15 (commercial name of Rohm and Haas Company), 8.0 ml of THF, 0.95 g (5.0 mmol) of tin (II) chloride and 2.0 ml of pure water were added to a 50-ml round-bottomed flask equipped with a condenser tube to provide a mixture, followed by reaction at 70° C. for 5 hours. After completion of the reaction, the reaction solution was filtered under reduced pressure and mixed with 40 ml of pure water, to which 50 ml of diethyl ether was added for extraction. The extraction was repeated three times.

Anhydrous magnesium sulfate was added to the organic phase obtained after the extraction for drying, and the solvent was distilled off from the solution obtained after filtration under reduced pressure to obtain 1.5 g of a colorless solid. The results of NMR measurement of the solid are indicated below. From the results, it was confirmed that the colorless solid was an intermediate compound (C3) (yield: 94%).

$^1$H-NMR (DMSO-d6) δ: 1.3-1.8 (m, 8H), 2.62 (m, 1H), 3.04 (s, 1H), 3.81 (s, 3H), 4.05 (t, 2H), 4.54 (m, 1H), 5.70 (s, 1H), 6.01 (s, 1H), 7.03 (d, 2H), 7.89 (d, 2H).

35 ml of ethanol, 1.5 g (4.7 mmol) of the compound (C3) obtained above and 5 ml of a 10% sodium hydroxide aqueous solution were added to a 100-ml round-bottomed flask equipped with a condenser tube to provide a mixture, followed by reaction under agitation at 85° C. for 3 hours. After completion of the reaction, 300 ml of water and the reaction solution were added to a 500-ml beaker and agitated at room temperature for 30 minutes, followed by dropping 5 ml of a 10% HCl aqueous solution and filtration to obtain 1.3 g of a white solid.

Next, 1.1 g of the resulting white solid, 1.0 g of Amberlyst (registered tradename) 15 (commercial name of Rohm and Haas Company), and 20.0 ml of THF were added to a 50-ml round-bottomed flask equipped with a condenser tube to provide a mixture, followed by reaction under agitation at 70° C. for 5 hours. After completion of the reaction, the solvent was distilled off from the solution obtained after the filtration of the reaction solution to obtain a yellow solid. This yellow solid was purified by re-crystallization (hexane/ethyl acetate=1/1) to obtain 0.9 g of a white solid. The results of NMR measurement of the solid are indicated below. From the results, it was confirmed that the white solid was an intended polymerizable liquid crystal compound (D3) (yield: 71%).

$^1$H-NMR (DMSO-d6) δ: 1.2-1.8 (m, 8H), 2.60 (m, 1H), 3.09 (m, 1H), 4.04 (m, 2H), 4.55 (m, 1H), 5.69 (s, 1H), 6.02 (s, 1H), 6.99 (d, 2H), 7.88 (d, 2H), 12.5 (s, broad, 1H).

[Chemical Formula 48]

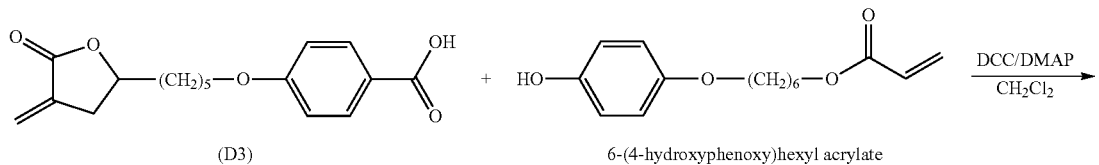

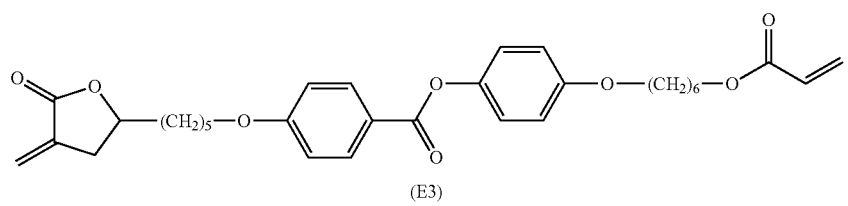

6.1 g (20.0 mmol) of the compound (D3) obtained above, 5.3 g (20.0 mmol) of 4-[(6-acryloxy)hexyloxy]phenol, 0.1 g of N,N-dimethyl-4-aminopyridine (hereinafter referred to as DMAP) and a small amount of BHT were suspended in 100 ml of methylene chloride under agitation at room temperature, to which a solution dissolving 5.1 g (25.0 mmol) of dicyclohexylcarbodiimide (hereinafter referred to as DCC) was added and agitated overnight. The resulting precipitate of DCC urea was separated by filtration and the filtrate was successively washed each twice with 100 ml of 0.5-N HCl, 100 ml of a saturated sodium hydrogen carbonate aqueous solution and 150 ml of a saturated saline solution, followed by drying with magnesium sulfate and distilling off the solvent under reduced pressure to obtain a yellow solid. This solid was purified by silica gel column chromatography (column: silica gel 60, 0.063 to 0.200 mm, made by Merck KGaA, eluate: hexane/ethyl acetate=1/1). The solvent was distilled off from the resulting solution to obtain 4.3 g of an intended polymerizable liquid crystal compound (E3) (yield: 39%).

$^1$H-NMR (CDCl$_3$) δ: 1.53 (m, 10H), 1.72 (m, 2H), 1.79 (m, 4H), 2.58 (m, 1H), 3.07 (m, 1H), 3.96 (t, 2H), 4.05 (t, 2H), 4.18 (t, 2H), 4.54 (m, 1H), 5.64 (d, 1H), 5.81 (d, 1H), 6.14 (m, 1H), 6.24 (d, 1H), 6.40 (d, 1H), 6.97 (m, 4H), 7.09 (d, 2H), 8.14 (d, 2H).

It will be noted that the observation of the liquid phase of the polymerizable liquid crystal compound (E3) revealed that it was converted to an isotropic liquid state at 59° C. in the course of raising the temperature. In the course of descending the temperature, phase transition to a smectic X phase took place at 55° C.

Example 1

Synthesis of Polymerizable Liquid Crystal Compound (Z1)

[Chemical Formula 49]

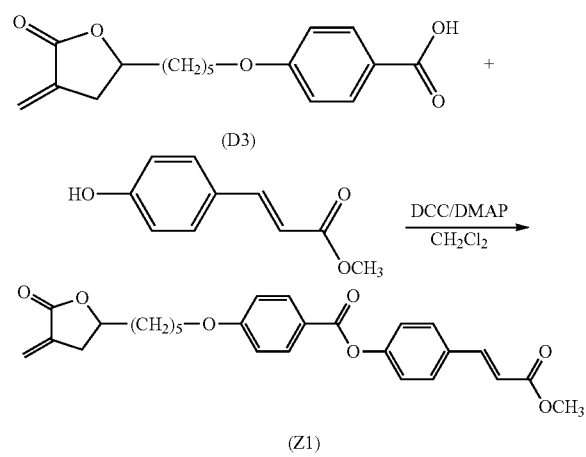

3.0 g (10.0 mmol) of the compound (D3) obtained above, 1.8 g (10.0 mmol) of methyl 4-hydroxycinnamate, 0.05 g of DMAP and a small amount of BHT were suspended in 60 ml of methylene chloride under agitation at room temperature, to which a solution dissolving 2.7 g (13.0 mmol) of DCC was added and agitated overnight. The resulting precipitate of DCC urea was separated by filtration and the filtrate was successively washed each twice with 150 ml of 0.5-N HCl, 50 ml of a saturated sodium hydrogen carbonate aqueous solution and 100 ml of a saturated saline solution, followed by drying with magnesium sulfate and distilling off the solvent under reduced pressure to obtain a yellow solid. This solid was purified by re-crystallization from ethanol to obtain 2.6 g of an intended polymerizable liquid crystal compound (Z1) (yield: 56%).

$^1$H-NMR (CDCl$_3$) δ: 1.40-1.90 (m, 8H), 2.58 (m, 1H), 3.08 (m, 1H), 3.80 (s, 3H), 4.05 (t, 2H), 4.55 (m, 1H), 5.64 (s, 1H), 6.22 (s, 1H), 6.42 (d, 1H), 6.97 (d, 2H), 7.22 (d, 2H), 7.60 (d, 2H), 7.70 (d, 1H), 8.15 (d, 2H).

It will be noted that the observation of the liquid crystalline phase of the polymerizable liquid crystal compound (Z1) revealed that it was converted to an isotropic liquid state at 137° C. in the course of raising the temperature. In the course of descending the temperature, phase transition to a nematic phase took place at 130° C.

Example 2

Synthesis of Polymerizable Liquid Crystal Compound (Z2)

[Chemical Formula 50]

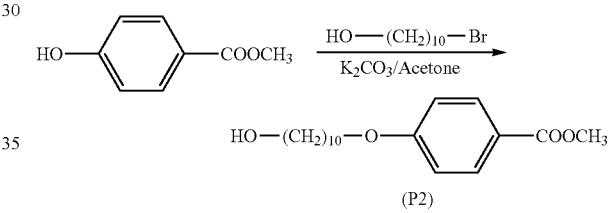

16.0 g (105.0 mmol) of methyl 4-hydroxybenzoate, 25.0 g (105.0 mmol) of 10-bromo-1-decanol, 29.0 g (210.0 mmol) of potassium carbonate and 200 ml of acetonitrile were added to a 200-ml round-bottomed flask equipped with a condenser tube to provide a mixture, followed by reaction under agitation at 80° C. for 48 hours. After completion of the reaction, the solution was filtered under reduced pressure and the solvent was distilled off to obtain a yellow wet solid. This solid was purified by silica gel column chromatography (column: silica gel 60, 0.063 to 0.200 mm, made by Merck KGaA, eluate: hexane/ethyl acetate=1/1). The solvent was distilled off from the resulting solution to obtain 21.4 g of a white solid. The results of NMR measurement of the solid are indicated below. From the results, it was confirmed that this white solid was an intermediate compound (P2) (yield: 66%)

$^1$H-NMR (CDCl$_3$) δ: 1.2-1.6 (m, 14H), 1.8 (m, 2H), 3.63 (t, 2H), 3.88 (s, 3H), 4.02 (t, 2H), 6.90 (d, 2H), 7.99 (d, 2H).

[Chemical Formula 51]

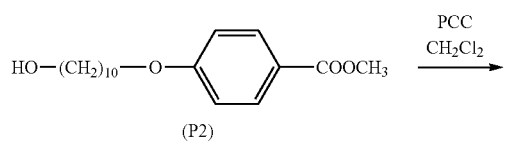

-continued

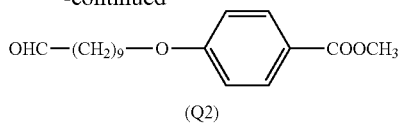

(Q2)

Next, 15.0 g (69.5 mmol) of PCC and 100.0 ml of CH$_2$Cl$_2$ were added to a 500-ml three-necked flask equipped with a condenser tube, in which a solution of 21.4 g (69.5 mmol) of the intermediate compound (P3) obtained above in CH$_2$Cl$_2$ (100.0 ml) was dropped while mixing under agitation, followed by further agitation at room temperature for 6 hours. Subsequently, to the solution which was separated from an oily matter attached to the walls of the flask, 200 ml of diethyl ether was added and filtered under reduced pressure, followed by distilling off the solvent under reduced pressure to obtain a dark green wet solid.

This solid was purified according to silica gel column chromatography (column: silica gel 60, 0.063 to 0.200 mm, made by Merck KGaA, eluate: hexane/ethyl acetate=2/1). The solvent was distilled off from the resulting solution to obtain 16.2 g of a colorless solid. The results of NMR measurement of the solid are indicated below. From the results, it was confirmed that the colorless solid was an intermediate compound (Q2) (yield: 76%).

$^1$H-NMR (CDCl$_3$) δ: 1.26 (m, 10H), 1.62 (m, 2H), 1.79 (m, 2H), 2.42 (m, 2H), 3.88 (s, 3H), 4.00 (t, 2H), 6.91 (d, 2H), 7.99 (d, 2H), 9.76 (s, 1H).

[Chemical Formula 52]

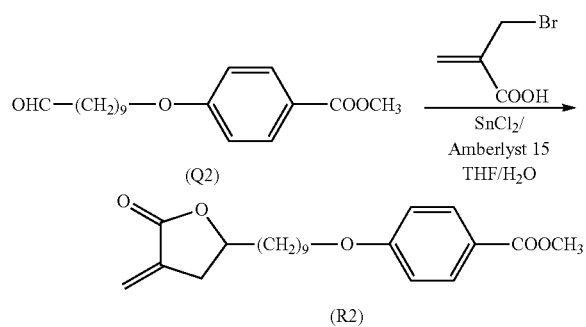

Next, 16.2 g (53.0 mmol) of the intermediate compound (Q2) obtained above, 8.8 g (53.0 mmol) of 2-(bromomethyl)acrylic acid, 7.4 g of Amberlyst (registered tradename) 15 (commercial name of Rohm and Haas Company), 85.0 ml of THF, 10.1 g (53.0 mmol) of tin (II) chloride and 20.0 ml of pure water were added to a 300-ml round-bottomed flask equipped with a condenser tube to provide a mixture, followed by reaction at 70° C. for 20 hours. After completion of the reaction, the reaction solution was filtered under reduced pressure and mixed with 100 ml of pure water, to which 100 ml of diethyl ether was added for extraction. The extraction was repeated three times.

Anhydrous magnesium sulfate was added to the organic phase obtained after the extraction so as to dry the organic phase, and the solvent was distilled off from the solution obtained after filtration under reduced pressure to obtain 16.4 g of a colorless solid. The results of NMR measurement of this solid are indicated below. From the results, it was confirmed that the colorless solid was the intended polymerizable liquid crystal compound (R2) (yield: 83%).

$^1$H-NMR (CDCl$_3$) δ: 1.28 (m, 12H), 1.60 (m, 2H), 1.72 (m, 2H), 2.51 (m, 1H), 3.06 (m, 1H), 3.85 (s, 3H), 4.04 (t, 2H), 4.54 (m, 1H), 5.69 (s, 1H), 6.02 (s, 1H), 7.01 (d, 2H), 7.88 (d, 2H).

[Chemical Formula 53]

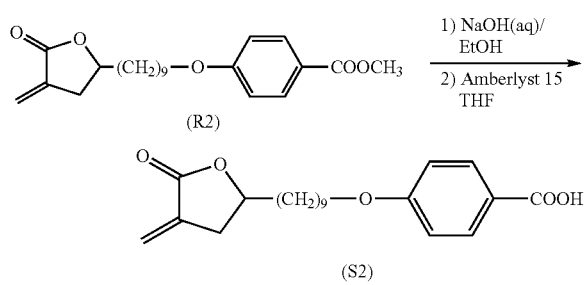

100 ml of ethanol, 16.4 g (43.8 mmol) of the compound (R2) obtained above and 60 ml of a 10% sodium hydroxide aqueous solution were added to a 500-ml round-bottomed flask equipped with a condenser tube to provide a mixture, followed by reaction under agitation at 85° C. for 5 hours. After completion of the reaction, 1000 ml of water and the reaction solution were added to a 2000-ml beaker and agitated at room temperature for 30 minutes, followed by dropping 60 ml of a 10% HCl aqueous solution and filtration to obtain 14.6 g of a white solid.

Next, 14.6 g of the resulting white solid, 8.0 g of Amberlyst (registered tradename) 15 (commercial name of Rohm and Haas Company), and 100 ml of THF were added to a 300-ml round-bottomed flask equipped with a condenser tube to provide a mixture, followed by reaction under agitation at 70° C. for 5 hours. After completion of the reaction, the solvent was distilled off from the solution obtained after the filtration of the reaction solution to obtain a yellow solid. This yellow solid was purified by re-crystallization (hexane/THF=2/1) to obtain 11.6 g of a white solid. The results of NMR measurement of the solid are indicated below. From the results, it was confirmed that the white solid was a compound (S2) (yield: 73%).

$^1$H-NMR (DMSO-d6) δ: 1.32 (m, 12H), 1.60 (m, 2H), 1.80 (m, 2H), 2.59 (m, 1H), 3.02 (m, 1H), 4.00 (t, 2H), 4.50 (m, 1H), 5.61 (s, 1H), 6.02 (s, 1H), 6.90 (d, 2H), 7.98 (d, 2H).

[Chemical Formula 54]

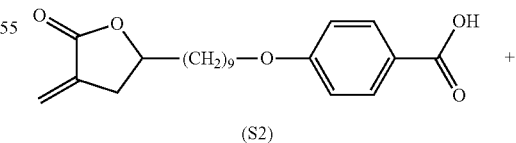

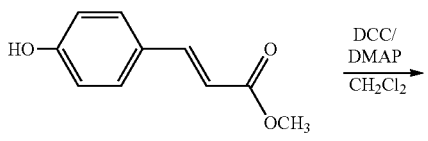

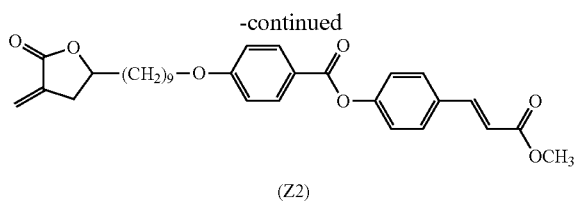

(Z2)

0.7 g (2.0 mmol) of the compound (S2) obtained above, 0.4 g (2.0 mmol) of methyl 4-hydroxycinnamate, 0.02 g of DMAP and a small amount of BHT were suspended in 10 ml of methylene chloride under agitation at room temperature, to which a solution dissolving 0.5 g (2.2 mmol) of DCC was added and agitated overnight. The resulting precipitate of DCC urea was separated by filtration and the filtrate was successively washed each twice with 50 ml of 0.5-N HCl, 50 ml of a saturated sodium hydrogen carbonate aqueous solution and 100 ml of a saturated saline solution, followed by drying with magnesium sulfate and distilling off the solvent under reduced pressure to obtain a yellow solid. This solid was purified by re-crystallization from ethanol to obtain 0.5 g of a white solid. The results of NMR measurement of this solid are indicated below. From the results, it was confirmed that the white solid was compound (Z2) (yield: 50%).

$^1$H-NMR (CDCl$_3$) δ: 1.30-1.90 (m, 16H), 2.58 (m, 1H), 3.05 (m, 1H), 3.80 (s, 3H), 4.05 (t, 2H), 4.50 (m, 1H), 5.62 (s, 1H), 6.22 (s, 1H), 6.40 (d, 1H), 6.98 (d, 2H), 7.22 (d, 2H), 7.60 (d, 2H), 7.70 (d, 1H), 8.18 (d, 2H).

It will be noted that the observation of the liquid crystalline phase of the polymerizable liquid crystal compound (Z2) revealed that it underwent phase transition to a smectic A phase at 60° C., to a nemactic phase at 89° C. and to an isotropic liquid state at 106° C. in the course of raising the temperature.

Example 3

Synthesis of Polymerizable Liquid Crystal Compound (Z3)

[Chemical Formula 55]

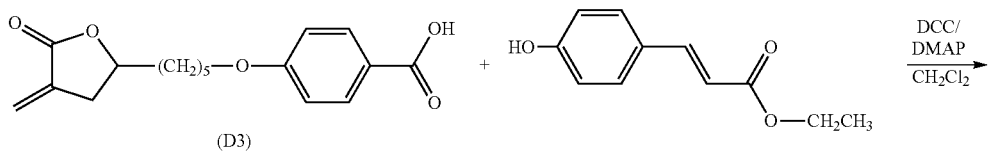

(D3)

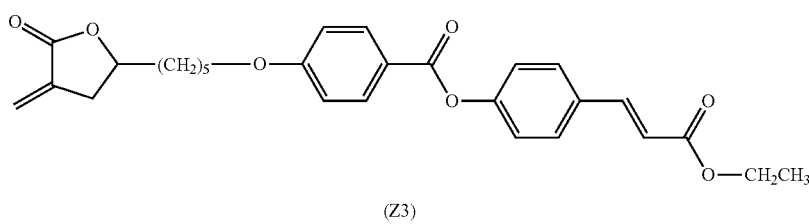

(Z3)

7.6 g (25.0 mmol) of the compound (D3) obtained above, 4.8 g (25.0 mmol) of ethyl 4-hydroxycinnamate, 0.1 g of DMAP and a small amount of BHT were suspended in 100 ml of methylene chloride under agitation at room temperature, to which a solution dissolving 6.7 g (32 mmol) of DCC was added and agitated overnight. The resulting precipitate of DCC urea was separated by filtration and the filtrate was successively washed each twice with 150 ml of 0.5-N HCl, 50 ml of a saturated sodium hydrogen carbonate aqueous solution and 100 ml of a saturated saline solution, followed by drying with magnesium sulfate and distilling off the solvent under reduced pressure to obtain a yellow solid. This solid was purified by re-crystallization from ethanol to obtain 7.1 g of a white solid. The results of NMR measurement of the solid are indicated below. From the results, it was confirmed that the solid was compound (Z3) (yield: 59%).

$^1$H-NMR (CDCl$_3$) δ: 1.35 (t, 3H), 1.40-1.90 (m, 8H), 2.60 (m, 1H), 3.08 (m, 1H), 4.05 (t, 2H), 4.25 (m, 2H), 4.55 (m, 1H), 5.64 (s, 1H), 6.22 (s, 1H), 6.40 (d, 1H), 6.97 (d, 2H), 7.22 (d, 2H), 7.60 (d, 2H), 7.70 (d, 1H), 8.15 (d, 2H).

It will be noted that the observation of the liquid crystalline phase of the polymerizable liquid crystal compound (Z3) revealed that it was converted to an isotropic liquid state at 96° C. in the course of raising the temperature. In the course of descending the temperature, phase transition to a nemactic phase at 91° C. and also to a smectic A phase at 77° C. took place.

Example 4

Synthesis of Polymerizable Liquid Crystal Compound (Z4)

[Chemical Formula 56]

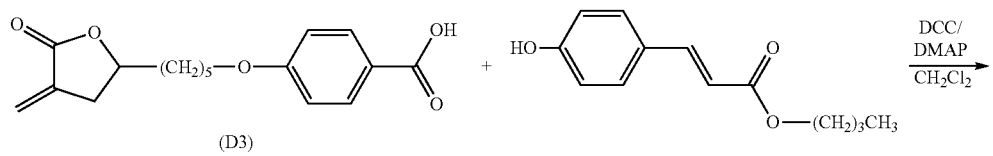

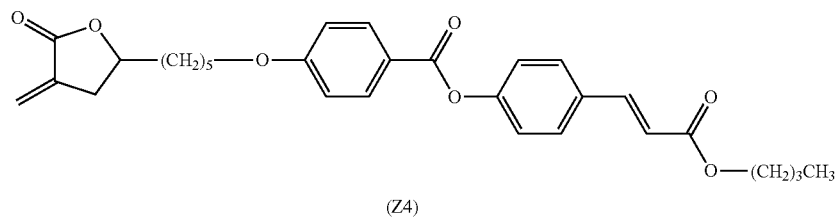

5.0 g (16.0 mmol) of the compound (D3) obtained above, 3.5 g (16.0 mmol) of butyl 4-hydroxycinnamate, 0.1 g of DMAP and a small amount of BHT were suspended in 64 ml of methylene chloride under agitation at room temperature, to which a solution dissolving 4.4 g (21 mmol) of DCC was added and agitated overnight. The resulting precipitate of DCC urea was separated by filtration and the filtrate was successively washed each twice with 50 ml of 0.5-N HCl, 50 ml of a saturated sodium hydrogen carbonate aqueous solution and 100 ml of a saturated saline solution, followed by drying with magnesium sulfate and distilling off the solvent under reduced pressure to obtain a yellow solid. This solid was purified by re-crystallization from ethanol to obtain 2.1 g of a white solid. The results of NMR measurement of the solid are indicated below. From the results, it was confirmed that the solid was compound (Z4) (yield: 26%).

$^1$H-NMR (CDCl$_3$) δ: 0.95 (t, 3H), 1.40-1.90 (m, 12H), 2.60 (m, 1H), 3.05 (m, 1H), 4.05 (t, 2H), 4.22 (m, 2H), 4.55 (m, 1H), 5.64 (s, 1H), 6.25 (s, 1H), 6.40 (d, 1H), 6.97 (d, 2H), 7.22 (d, 2H), 7.60 (d, 2H), 7.68 (d, 1H), 8.15 (d, 2H).

It will be noted that the observation of the liquid crystalline phase of the polymerizable liquid crystal compound (Z4) revealed that it was converted to an isotropic liquid state at 72° C. in the course of raising the temperature. In the course of descending the temperature, phase transition to a smectic A phase at 47° C. took place.

Example 5

Synthesis of Polymerizable Liquid Crystal Compound (Z5)

0.30 g (1.0 mmol) of the compound (D3) obtained above, 0.25 g (1.0 mmol) of E-3-(4'-hydroxybiphenyl-4-yl)acrylic acid, 0.01 g of DMAP and a small amount of BHT were suspended in 5.0 ml of methylene chloride under agitation at room temperature, to which a solution dissolving 0.27 g (1.3 mmol) of DCC was added and agitated overnight. The resulting precipitate of DCC urea was separated by filtration and the filtrate was successively washed each twice with 20 ml of 0.5N HCl, 20 ml of a saturated sodium hydrogen carbonate aqueous solution and 50 ml of a saturated saline solution, followed by drying with magnesium sulfate and distilling off the solvent under reduced pressure to obtain a yellow solid. This solid was purified by re-crystallization from ethanol to obtain 0.40 g of a white solid. The results of NMR measurement of the solid are indicated below. From the results, it was confirmed that the white solid was compound (Z5) (yield: 74%).

$^1$H-NMR (CDCl$_3$) δ: 1.55 (m, 6H), 1.90 (m, 2H), 2.60 (m, 1H), 3.05 (m, 1H), 3.85 (s, 3H), 4.05 (t, 2H), 4.55 (m, 1H), 5.64 (s, 1H), 6.25 (s, 1H), 6.45 (d, 1H), 6.98 (d, 2H), 7.25 (m, 4H), 7.65 (m, 4H), 7.75 (d, 1H), 8.15 (d, 2H).

It will be noted that the observation of the liquid crystalline phase of the polymerizable liquid crystal compound (Z5) revealed that it underwent phase transition to a smectic phase at 100° C. and was polymerized at >130° C. in the course of raising the temperature.

[2] Polymerizable Liquid Crystal Composition and Polymerized Product Thereof (Film)

The compounds used in the following examples and comparative examples are just as indicated below. The compositions of Examples 6 to 14 and Comparative Example 1 are shown in Table 1 (unit: mg).

[Chemical Formula 57]

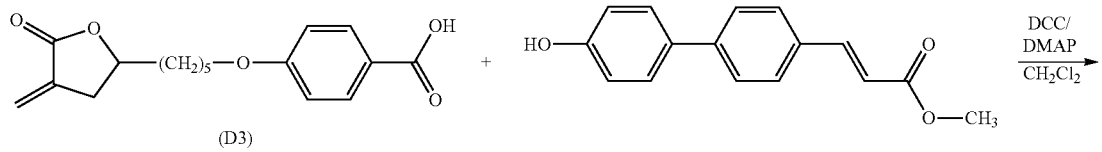

(D3)

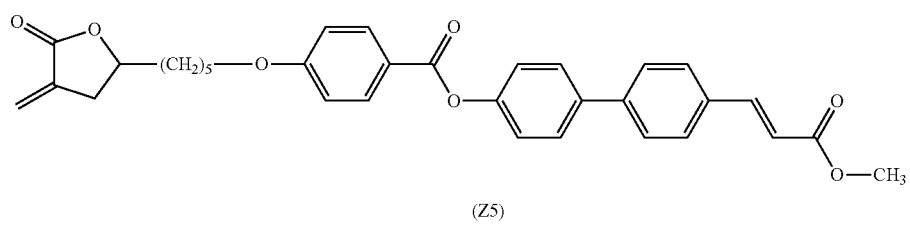

(Z5)

[Chemical Formula 58]

(E1) NC–C6H4–C6H4–O–(CH2)3–O–C(=O)–CH=CH2

(E2) (methylene-γ-butyrolactone)–(CH2)5–O–C6H4–C6H4–CN (E3) (methylene-γ-butyrolactone)–(CH2)5–O–C6H4–C(=O)–O–C6H4–O–(CH2)6–O–C(=O)–CH=CH2

(Z1) (methylene-γ-butyrolactone)–(CH2)5–O–C6H4–C(=O)–O–C6H4–CH=CH–C(=O)–OCH3

(Z2) (methylene-γ-butyrolactone)–(CH2)9–O–C6H4–C(=O)–O–C6H4–CH=CH–C(=O)–OCH3

(Z3) (methylene-γ-butyrolactone)–(CH2)5–O–C6H4–C(=O)–O–C6H4–CH=CH–C(=O)–O–CH2CH2

(Z4) (methylene-γ-butyrolactone)–(CH2)5–O–C6H4–C(=O)–O–C6H4–CH=CH–C(=O)–O–(CH2)3CH3

TABLE 1

| | Compound E1 | Compound E2 | Compound E3 | Compound Z1 | Compound Z2 | Compound Z3 | Compound Z4 |
|---|---|---|---|---|---|---|---|
| Example 6 | — | — | — | — | — | 100.0 | — |
| Example 7 | 45.0 | 45.0 | 45.0 | 15.0 | — | — | — |
| Example 8 | 45.0 | 30.0 | 45.0 | 30.0 | — | — | — |
| Example 9 | 15.0 | 15.0 | 45.0 | 75.0 | — | — | — |
| Example 10 | — | — | 45.0 | 105.0 | — | — | — |
| Example 11 | 45.0 | 30.0 | 45.0 | — | — | 30.0 | — |
| Example 12 | 60.0 | 60.0 | 90.0 | — | — | 90.0 | — |
| Example 13 | 45.0 | 30.0 | 45.0 | — | — | — | 30.0 |
| Example 14 | 45.0 | 30.0 | 45.0 | — | 30.0 | — | — |
| Comparative Example 1 | 60.0 | 45.0 | 45.0 | — | — | — | — |

Example 6

Polymerizable Liquid Crystal Composition and its Polymerized Product (Film)

100.0 mg of the polymerizable liquid crystal compound (Z3), 2.0 mg of Irgacure 369 (commercial name), made by Ciba Geigy K. K., serving as a photopolymerizable initiator, and 0.2 mg of R-30 surfactant (made by DIC corporation) were dissolved in 0.40 g of cyclohexanone to obtain a polymerizable liquid crystal composition.

This polymerizable liquid crystal composition was coated onto a liquid crystal orientation film surface of a liquid crystal orientation film-bearing substrate by spin coating (1000 rpm, 20 seconds) and pre-baked on a hot plate at 100° C. for 60 seconds, followed by allowing to cool down to room temperature. On this occasion, the polymerizable composition on the substrate was left as a liquid crystal state. The liquid crystal orientation film-bearing substrate used herein was one wherein an liquid crystal orienting agent (SE-1410, made by Nissan Chemical Industries, Ltd.) was coated onto an ITO surface of an ITO-coated glass substrate by spin coating and baked at 230° C. to form a 100-nm thick thin film, followed by rubbing.

Next, the film formed on the liquid crystal orientation film-bearing substrate was irradiated in air with light having an intensity of 1000 mJ/cm$^2$ by use of a mercury lamp to cause the polymerizable liquid crystal composition to be polymerized.

The resulting film had a thickness of 0.86 μm and it was confirmed by observation through a polarizing microscope that the film was oriented horizontally along the substrate surface. The retardation value was at 49 nm and the haze value was at 0.00. The value of $\Delta n$ (400 nm)/$\Delta n$ (550 nm) was at 1.22.

Example 7

Polymerizable Liquid Crystal Composition and its Polymerized Product (Film)

45.0 mg of the polymerizable liquid crystal compound (E1), 45.0 mg of the polymerizable liquid crystal compound (E2), 45.0 mg of the polymerizable liquid crystal compound (E3), 15.0 mg of the polymerizable liquid crystal compound (Z1), 3.0 mg of Irgacure 369 (commercial name), made by Ciba Geigy K. K., serving as a photopolymerizable initiator, 0.3 mg of R-30 surfactant (made by DIC corporation) were dissolved in 0.35 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.78 μm and it was confirmed by observation through a polarizing microscope that the film was oriented horizontally along the substrate surface. The retardation value was at 234 nm and the haze value was at 0.16. The value of $\Delta n$ (400 nm)/$\Delta n$ (550 nm) was at 1.25.

Example 8

Polymerizable Liquid Crystal Composition and its Polymerized Product (Film)

45.0 mg of the polymerizable liquid crystal compound (E1), 30.0 mg of the polymerizable liquid crystal compound (E2), 45.0 mg of the polymerizable liquid crystal compound (E3), 30.0 mg of the polymerizable liquid crystal compound (Z1), 3.0 mg of Irgacure 369 (commercial name), made by Ciba Geigy K. K., serving as a photopolymerizable initiator, and 0.3 mg of R-30 surfactant (made by DIC corporation) were dissolved in 0.35 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.74 μm and it was confirmed by observation through a polarizing microscope that the film was oriented horizontally along the substrate surface. The retardation value was at 229 nm and the haze value was at 0.40. The value of $\Delta n$ (400 nm)/$\Delta n$ (550 nm) was at 1.24.

Example 9

Polymerizable Liquid Crystal Composition and its Polymerized Product (Film)

15.0 mg of the polymerizable liquid crystal compound (E1), 15.0 mg of the polymerizable liquid crystal compound (E2), 45.0 mg of the polymerizable liquid crystal compound (E3), 75.0 mg of the polymerizable liquid crystal compound (Z1), 3.0 mg of Irgacure 369 (commercial name), made by Ciba Geigy K. K., serving as a photopolymerizable initiator, and 0.3 mg of R-30 surfactant (made by DIC corporation) were dissolved in 0.35 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.72 μm and it was confirmed by observation through a polarizing microscope that the film was oriented horizontally along the substrate surface. The retardation value was at 189 nm and the haze value was at 0.08. The value of $\Delta n$ (400 nm)/$\Delta n$ (550 nm) was at 1.22.

Example 10

Polymerizable Liquid Crystal Composition and its Polymerized Product (Film)

45.0 mg of the polymerizable liquid crystal compound (E3), 105.0 mg of the polymerizable liquid crystal compound (Z1), 3.0 mg of Irgacure 369 (commercial name), made by Ciba Geigy K. K., serving as a photopolymerizable initiator, and 0.3 mg of R-30 surfactant (made by DIC corporation) were dissolved in 0.35 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.74 μm and it was confirmed by observation through a polarizing microscope that the film was oriented horizontally along the substrate surface. The retardation value was at 177 nm and the haze value was at 0.47. The value of $\Delta n$ (400 nm)/$\Delta n$ (550 nm) was at 1.20.

Example 11

Polymerizable Liquid Crystal Composition and its Polymerized Product (Film)

45.0 mg of the polymerizable liquid crystal compound (E1), 30.0 mg of the polymerizable liquid crystal compound (E2), 45.0 mg of the polymerizable liquid crystal compound (E3), 30.0 mg of the polymerizable liquid crystal compound (Z3), 3.0 mg of Irgacure 369 (commercial name), made by Ciba Geigy K. K., serving as a photopolymerizable initiator, and 0.3 mg of R-30 surfactant (made by DIC corporation) were dissolved in 0.35 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.70 μm and it was confirmed by observation through a polarizing microscope that the film was oriented horizontally along the substrate surface. The retardation value was at 193 nm and the haze value was at 0.08. The value of $\Delta n$ (400 nm)/$\Delta n$ (550 nm) was at 1.24.

Example 12

Polymerizable Liquid Crystal Composition and its Polymerized Product (Film)

60.0 mg of the polymerizable liquid crystal compound (E1), 60.0 mg of the polymerizable liquid crystal compound (E2), 90.0 mg of the polymerizable liquid crystal compound (E3), 90.0 mg of the polymerizable liquid crystal compound (Z3), 6.0 mg of Irgacure 369 (commercial name), made by Ciba Geigy K. K., serving as a photopolymerizable initiator, and 0.6 mg of R-30 surfactant (made by DIC corporation) were dissolved in 0.70 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.69 and it was confirmed by observation through a polarizing microscope that the film was oriented horizontally along the substrate surface. The retardation value was at 221 nm and the haze value was at 0.13. The value of $\Delta n$ (400 nm)/$\Delta n$ (550 nm) was at 1.23.

Example 13

Polymerizable Liquid Crystal Composition and its Polymerized Product (Film)

45.0 mg of the polymerizable liquid crystal compound (E1), 30.0 mg of the polymerizable liquid crystal compound (E2), 45.0 mg of the polymerizable liquid crystal compound (E3), 30.0 mg of the polymerizable liquid crystal compound (Z4), 3.0 mg of Irgacure 369 (commercial name), made by Ciba Geigy K. K., serving as a photopolymerizable initiator, and 0.3 mg of R-30 surfactant (made by DIC corporation) were dissolved in 0.35 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.78 μm and it was confirmed by observation through a polarizing microscope that the film was oriented vertically relative to the substrate surface. The retardation value was at 45 nm (measuring angle: 50°) and the haze value was at 0.08.

Example 14

Polymerizable Liquid Crystal Composition and its Polymerized Product (Film)

45.0 mg of the polymerizable liquid crystal compound (E1), 30.0 mg of the polymerizable liquid crystal compound (E2), 45.0 mg of the polymerizable liquid crystal compound (E3), 30.0 mg of the polymerizable liquid crystal compound (Z2), 3.0 mg of Irgacure 369 (commercial name), made by Ciba Geigy K. K., serving as a photopolymerizable initiator, and 0.3 mg of R-30 surfactant (made by DIC corporation) were dissolved in 0.35 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.30 and it was confirmed by observation through a polarizing microscope that the film was oriented horizontally along the substrate surface. The retardation value was at 182 nm and the haze value was at 0.10. The value of $\Delta n$ (400 nm)/$\Delta n$ (550 nm) was at 1.22.

Comparative Example 1

Polymerizable Liquid Crystal Composition and its Polymerized Product (Film)

60.0 mg of the polymerizable liquid crystal compound (E1), 45.0 mg of the polymerizable liquid crystal compound (E2), 45.0 mg of the polymerizable liquid crystal compound (E3), 3.0 mg of Irgacure 369 (commercial name), made by Ciba Geigy K. K., serving as a photopolymerizable initiator, and 0.3 mg of R-30 surfactant (made by DIC corporation) were dissolved in 0.35 g of cyclohexanone to obtain a polymerizable liquid crystal composition.

Using this polymerizable liquid crystal composition, a film was obtained in the same manner as in Example 6. It will be noted that the composition on the substrate after the pre-baking was found to be a liquid crystal state.

The resulting film had a thickness of 1.74 and it was confirmed by observation through a polarizing microscope that the film was oriented horizontally along the substrate surface. The retardation value was at 217 nm and the haze value was at 0.08. The value of $\Delta n$ (400 nm)/$\Delta n$ (550 nm) was at 1.25.

Examples 6 to 14 and Comparative Example 1 were summarized in Table 2.

TABLE 2

| | Film thickness (μm) | $\Delta nD$ (nm) | $\Delta n(400)/\Delta n(550)$ | Haze value (%) |
|---|---|---|---|---|
| Example 6 | 0.86 | 49 | 1.22 | 0.00 |
| Example 7 | 1.78 | 234 | 1.25 | 0.16 |
| Example 8 | 1.74 | 229 | 1.24 | 0.40 |
| Example 9 | 1.72 | 189 | 1.22 | 0.08 |
| Example 10 | 1.74 | 177 | 1.20 | 0.47 |
| Example 11 | 1.70 | 193 | 1.24 | 0.08 |
| Example 12 | 1.69 | 221 | 1.23 | 0.13 |

TABLE 2-continued

| | Film thickness (μm) | ΔnD (nm) | Δn(400)/ Δn(550) | Haze value (%) |
|---|---|---|---|---|
| Example 13 | 1.78 | 45 | — | 0.08 |
| Example 14 | 1.30 | 182 | 1.22 | 0.10 |
| Comparative Example 1 | 1.74 | 217 | 1.25 | 0.08 |

* Δn(400)/Δn(550) = (ΔnD at λ = 400 nm)/(ΔnD at λ = 550 nm)
* The film of Example 13 was vertically oriented, so that the retardation value was measured at 50°.

Example 15

Polymerizable Liquid Crystal Composition and its Polymerized Product (Film)

Using the same polymerizable liquid crystal composition as in Example 7, spin coating and pre-baking were carried out in the same manner as in Example 6. It will be noted that the composition on the substrate after the pre-baking was in a liquid crystal state.

Next, the film formed on the liquid crystal orientation film-bearing substrate was masked on its half region and the other half was irradiated, in air, with light having an intensity of 1000 mJ/cm$^2$ by use of a mercury lamp to polymerize the polymerizing liquid crystal composition, followed by developing with PGMEA at room temperature for 10 seconds and further rinsing with PGMEA at room temperature for 10 seconds. Thereafter, it was confirmed that no non-exposed portion was observed.

On the other hand, the film obtained from the exposed portion had a thickness of 1.25 μm, and observation through a polarizing microscope revealed that the film was oriented horizontally along the substrate surface. The retardation value was at 155 nm and the haze value was at 0.11. The value of Δn (400 nm)/Δn (550 nm) was at 1.22.

Example 16

Polymerizable Liquid Crystal Composition and its Polymerized Product (Film)

Using the same polymerizable liquid crystal composition as in Example 8, the formation of an oriented film, light irradiation, development and rinsing were carried out in the same manner as in Example 15, and it was confirmed that no non-exposed portion was found. It will be noted that the composition on the substrate after the pre-baking was in a liquid crystal state.

The film obtained from the exposed portion had a thickness of 1.28 μm, and observation through a polarizing microscope revealed that the film was oriented horizontally along the substrate surface. The retardation value was at 178 nm and the haze value was at 0.32. The value of Δn (400 nm)/Δn (550 nm) was at 1.19.

Example 17

Polymerizable Liquid Crystal Composition and its Polymerized Product (Film)

Using the same polymerizable liquid crystal composition as in Example 9, the formation of an oriented film, light irradiation, development and rinsing were carried out in the same manner as in Example 15, and it was confirmed that no non-exposed portion was found. It will be noted that the composition on the substrate after the pre-baking was in a liquid crystal state.

The film obtained from the exposed portion had a thickness of 1.24 μm, and observation through a polarizing microscope revealed that the film was oriented horizontally along the substrate surface. The retardation value was at 152 nm and the haze value was at 0.16. The value of Δn (400 nm)/Δn (550 nm) was at 1.20.

Example 18

Polymerizable Liquid Crystal Composition and its Polymerized Product (Film)

Using the same polymerizable liquid crystal composition as in Example 12, the formation of an oriented film, light irradiation, development and rinsing were carried out in the same manner as in Example 15, and it was confirmed that no non-exposed portion was found. It will be noted that the composition on the substrate after the pre-baking was in a liquid crystal state.

The film obtained from the exposed portion had a thickness of 1.17 μm, and observation through a polarizing microscope revealed that the film was oriented horizontally along the substrate surface. The retardation value was at 147 nm and the haze value was at 0.08. The value of Δn (400 nm)/Δn (550 nm) was at 1.21.

Comparative Example 2

Polymerizable Liquid Crystal Composition and its Polymerized Product (Film)

Using the same polymerizable liquid crystal composition as in Comparative Example 1, the formation of an oriented film, light irradiation, development and rinsing were carried out in the same manner as in Example 15, and it was confirmed that no non-exposed portion was found. It will be noted that the composition on the substrate after the pre-baking was in a liquid crystal state.

The film obtained from the exposed portion had a thickness of 0.90 μm, and observation through a polarizing microscope revealed that the film was oriented horizontally along the substrate surface. The retardation value was at 107 nm and the haze value was at 0.08. The value of Δn (400 nm)/Δn (550 nm) was at 1.23.

Examples 15 to 18 and Comparative Example 2 were summarized in Table 3. It will be noted that for comparison with the evaluation of film loss after patterning, the results of Examples 7, 8, 9, 12 and Comparative Example 1 are also indicated in Table 3.

TABLE 3

| | Film thickness (μm) | ΔnD (nm) | Δn(400)/ Δn(550) | Haze value (%) |
|---|---|---|---|---|
| Example 7 (no development) | 1.78 (100%) | 234 (100%) | 1.25 | 0.16 |
| Example 15 (after development) | 1.25 (70%) | 155 (66%) | 1.22 | 0.11 |
| Example 8 (no development) | 1.74 (100%) | 229 (100%) | 1.24 | 0.40 |
| Example 16 (after development) | 1.28 (74%) | 178 (78%) | 1.19 | 0.32 |
| Example 9 (no development) | 1.72 (100%) | 189 (100%) | 1.22 | 0.08 |

TABLE 3-continued

| | Film thickness (μm) | ΔnD (nm) | Δn(400)/ Δn(550) | Haze value (%) |
|---|---|---|---|---|
| Example 17 (after development) | 1.24 (72%) | 152 (80%) | 1.20 | 0.16 |
| Example 12 (no development) | 1.69 (100%) | 221 (100%) | 1.23 | 0.13 |
| Example 18 (after development) | 1.17 (69%) | 147 (67%) | 1.21 | 0.08 |
| Comparative Example 1 (no development) | 1.74 (100%) | 217 (100%) | 1.25 | 0.08 |
| Comparative Example 2 (after development) | 0.90 (52%) | 107 (49%) | 1.23 | 0.08 |

* Δn(400)/Δn (550) = (ΔnD at λ = 400 nm)/(ΔnD at λ = 550 nm)

As shown in Table 3, it will be seen that those of Examples 15 to 18 including the polymerizable liquid crystal compositions of the present invention are more excellent in chemical resistance than that of Comparative Example 2 not containing such a composition and are suppressed in film loss after the development thereover.

The invention claimed is:

1. A polymerizable liquid crystal compound, characterized by being represented by the following formula [1]:

[Chemical Formula 1]

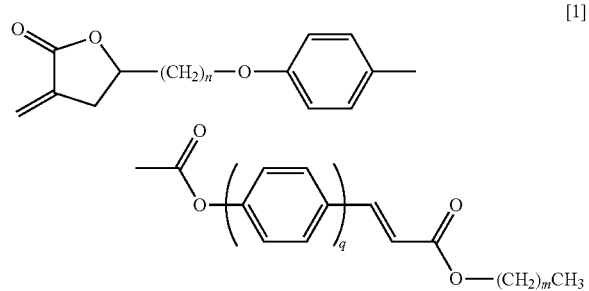

[1]

wherein n is an integer of 3 to 10, m is an integer of 0 to 5, and q is an integer of 1 to 2.

2. A polymerizable liquid crystal composition comprising the polymerizable liquid crystal compound defined in claim 1.

3. The polymerizable liquid crystal composition as defined in claim 2, further comprising a liquid crystal compound having at least one polymerizable group in the molecule.

4. The polymerizable liquid crystal composition as defined in claim 3, wherein said liquid crystal compound is a compound having at least one polymerizable group represented by the following formula [2] or [3] in the molecule.

[Chemical Formula 2]

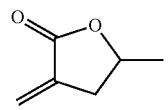

[2]

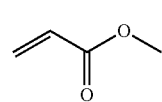

[3]

5. The polymerizable liquid crystal composition as defined in claim 3 or 4, wherein said liquid crystal compound is at least one selected from the group consisting of compounds represented by the following formula [4]:

[Chemical Formula 3]

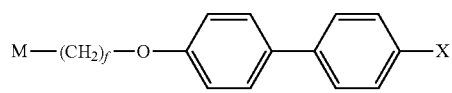

[4]

in which X is a fluorine atom, a cyano group or a monovalent hydrocarbon group having 4 to 8 carbon atoms, f represents an integer of 2 to 9, and M is a group represented by the following formula [2] or [3].

[Chemical Formula 4]

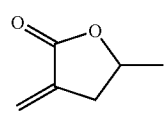

[2]

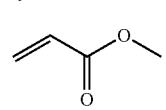

[3]

6. A polymer obtained by polymerizing a polymerizable liquid crystal composition comprising a polymerizable liquid crystal compound represented by the following formula [1]:

[Chemical Formula 1]

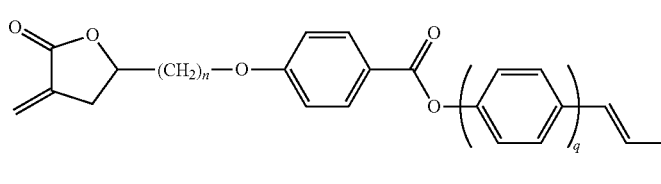

[1]

wherein n is an integer of 3 to 10, m is an integer of 0 to 5, and q is an integer of 1 to 2.

7. A film obtained by polymerizing a polymerizable liquid crystal composition comprising a polymerizable liquid crystal compound represented by the following formula [1]:

[Chemical Formula 1]

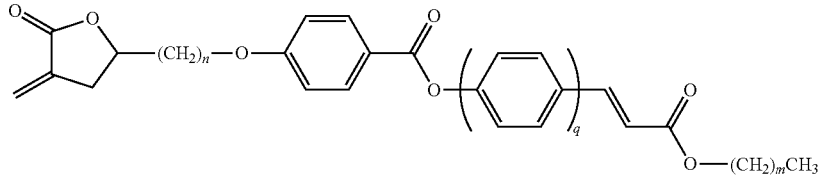

[1]

wherein n is an integer of 3 to 10, m is an integer of 0 to 5, and q is an integer of 1 to 2.

8. An oriented film obtained by polymerizing a polymerizable liquid crystal composition comprising a polymerizable liquid crystal compound represented by the following formula [1]:

[Chemical Formula 1]

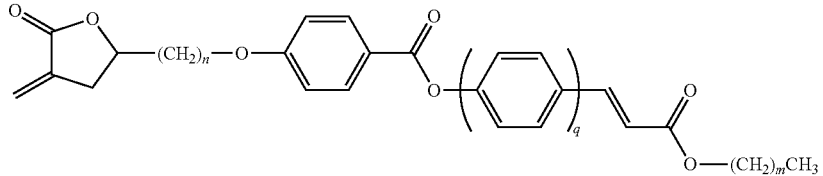

[1]

wherein n is an integer of 3 to 10, m is an integer of 0 to 5, and q is an integer of 1 to 2.

9. An optical device comprising the polymer defined in claim 6.

10. An optical device comprising the oriented film defined in claim 8.

* * * * *